(12) United States Patent
Makino et al.

(10) Patent No.: US 10,987,077 B2
(45) Date of Patent: *Apr. 27, 2021

(54) TOMOSYNTHESIS IMAGING APPARATUS AND METHOD FOR OPERATING THE SAME

(71) Applicant: FUJIFILM Corporation, Tokyo (JP)

(72) Inventors: Kazuhiro Makino, Kanagawa (JP); Masayoshi Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/579,861

(22) Filed: Sep. 24, 2019

(65) Prior Publication Data
US 2020/0100749 A1 Apr. 2, 2020

(30) Foreign Application Priority Data

Sep. 27, 2018 (JP) .............................. JP2018-182727

(51) Int. Cl.
*A61B 6/00* (2006.01)
*A61B 6/02* (2006.01)
*A61B 6/03* (2006.01)

(52) U.S. Cl.
CPC .............. *A61B 6/502* (2013.01); *A61B 6/025* (2013.01); *A61B 6/03* (2013.01); *A61B 6/4007* (2013.01); *A61B 6/4021* (2013.01); *A61B 6/54* (2013.01)

(58) Field of Classification Search
CPC ....... A61B 6/502; A61B 6/025; A61B 6/0414; A61B 6/107; A61B 6/4441; A61B 6/584; A61B 6/545; A61B 6/482; A61B 6/4417; A61B 6/027; A61B 6/4007; A61B 6/4411; A61B 6/5205; A61B 6/4452

See application file for complete search history.

(56) References Cited

U.S. PATENT DOCUMENTS

| 2009/0022264 | A1* | 1/2009 | Zhou | A61B 6/025 378/5 |
| 2009/0323893 | A1* | 12/2009 | Hanke | A61B 6/025 378/37 |
| 2011/0002441 | A1* | 1/2011 | Vogtmeier | A61B 6/4007 378/21 |

FOREIGN PATENT DOCUMENTS

| JP | 2016135319 | 7/2016 |
| WO | 2010028208 | 3/2010 |

* cited by examiner

*Primary Examiner* — Courtney D Thomas
(74) *Attorney, Agent, or Firm* — JCIPRNET

(57) ABSTRACT

A tomosynthesis imaging apparatus includes: a radiation detector having an imaging surface that detects radiation transmitted through an object and captures a projection image of the object; a radiation source that has a plurality of radiation tubes which emit the radiation to the imaging surface at different irradiation angles and selectively irradiates the object with the radiation from each of the plurality of radiation tubes; and a radiation source control unit that performs movement control for moving at least one of the plurality of radiation tubes to change the radiation irradiation angle of the radiation tube with respect to the imaging surface.

17 Claims, 24 Drawing Sheets

FIG. 10
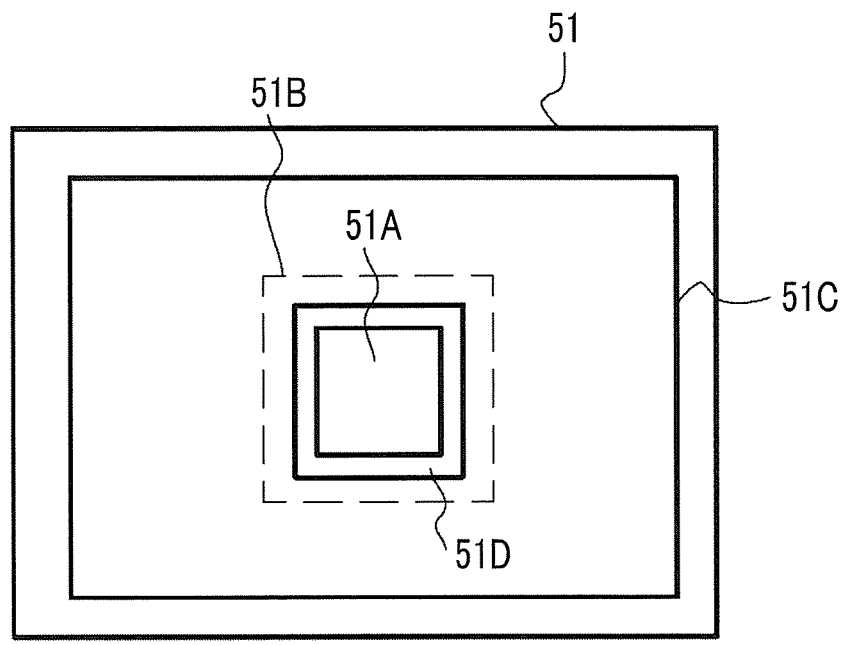
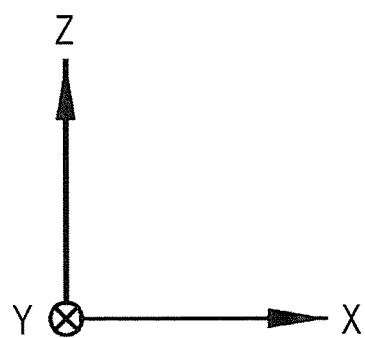

FIG. 11
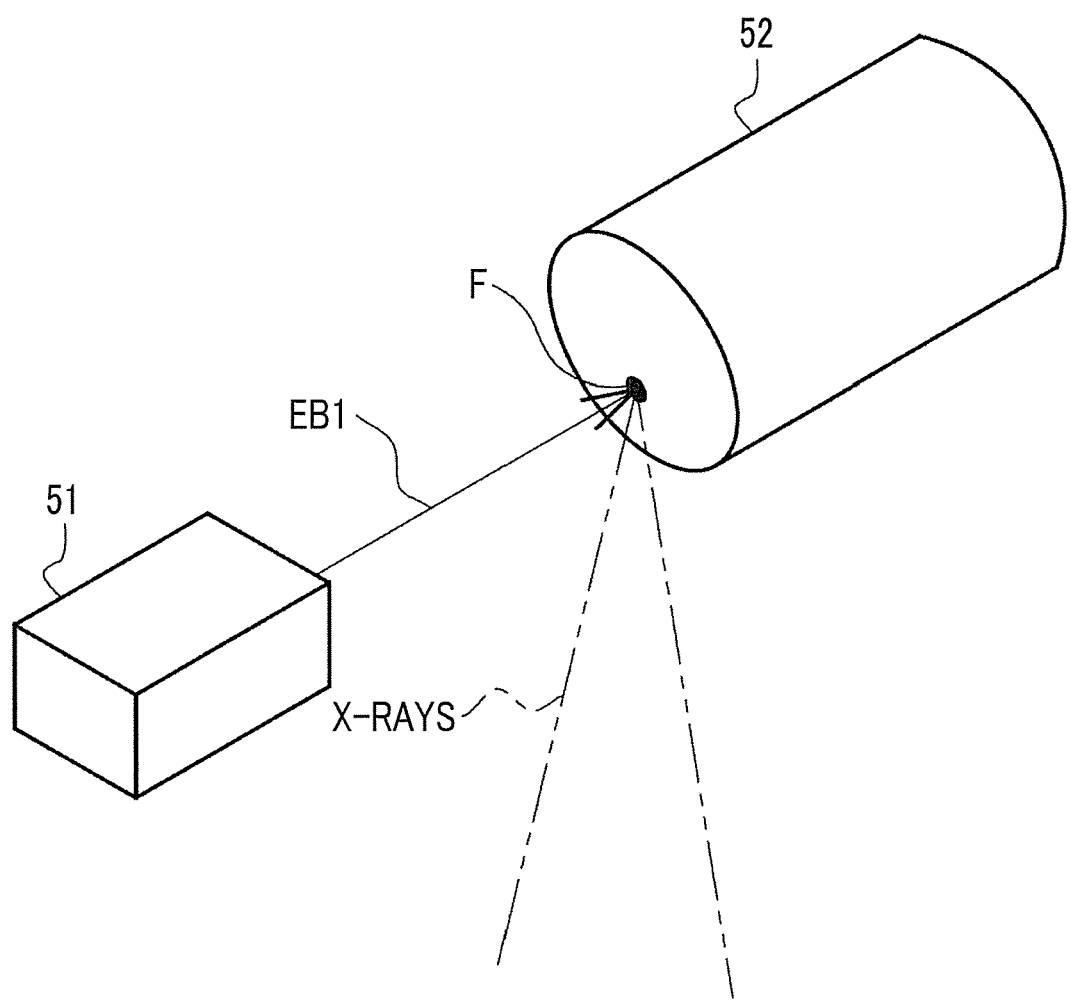
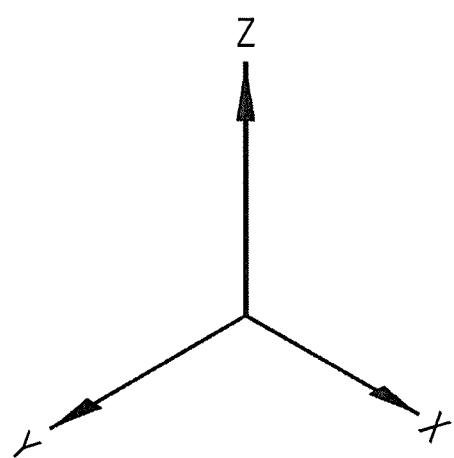

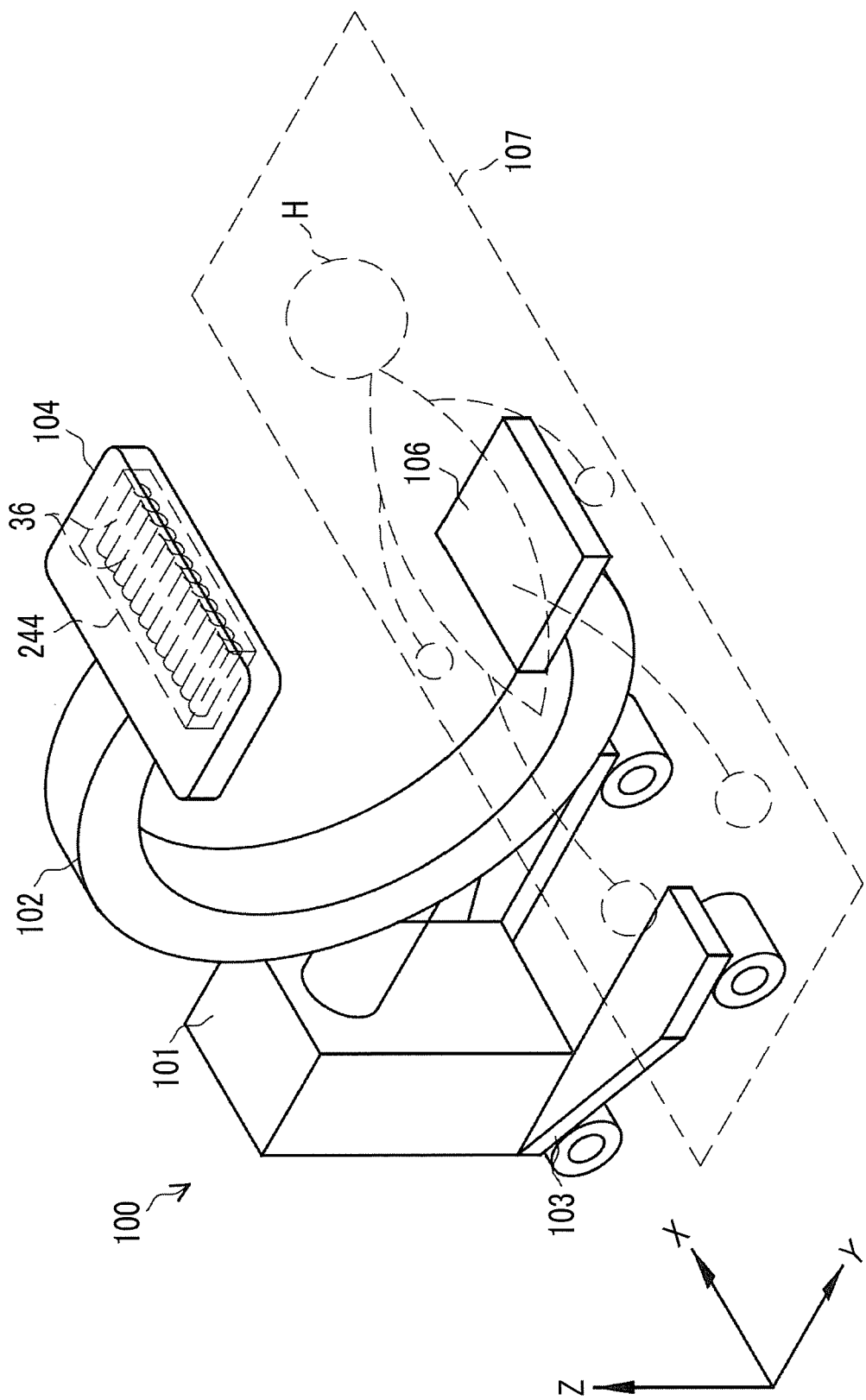

TOMOSYNTHESIS IMAGING APPARATUS AND METHOD FOR OPERATING THE SAME

CROSS-REFERENCE TO RELATED APPLICATIONS

The present application claims priority under 35 U.S.C. § 119 to Japanese Patent Application No. 2018-182727, filed on Sep. 27, 2018. The above application is hereby expressly incorporated by reference, in its entirety, into the present application.

BACKGROUND

1. Technical Field

The technology according to the present disclosure relates to a tomosynthesis imaging apparatus and a method for operating the same.

2. Description of the Related Art

In the medical field, an X-ray imaging apparatus using radiation, for example, X-rays has been known. A tomosynthesis imaging apparatus that can perform tomosynthesis imaging has been known as one of the X-ray imaging apparatuses. The tomosynthesis imaging apparatus comprises an X-ray detector, an X-ray source, and a movement mechanism for moving the X-ray source (for example, see JP2016-135319A). The X-ray detector has an image surface which is a two-dimensional plane as an imaging surface that detects X-rays transmitted through an object and captures a projection image of the object. The X-ray source includes one X-ray tube that irradiates the object with X-rays. The movement mechanism moves the X-ray source to change the irradiation angle of X-rays emitted from one X-ray tube with respect to the imaging surface.

In one tomosynthesis imaging operation, one X-ray tube emits X-rays at a plurality of different irradiation angles while being moved to acquire a plurality of projection images with different irradiation angles. A tomographic image of a tomographic plane at any position of the object is reconstructed on the basis of the plurality of acquired projection images. The tomosynthesis imaging is used for, for example, mammography using the breast as the object.

SUMMARY

The tomosynthesis imaging apparatus according to the related art, such as the tomosynthesis imaging apparatus disclosed in JP2016-135319A, performs tomosynthesis imaging while moving one X-ray tube. Therefore, the imaging time is longer than that in simple X-ray imaging which captures images in a state in which one X-ray tube is fixed. Moreover, in the tomosynthesis imaging, in addition to the movement of one X-ray tube, the X-ray tube may be stopped whenever X-rays are emitted, which also causes an increase in the imaging time.

Since the long imaging time is painful for the object, there is a demand to reduce the imaging time in the tomosynthesis imaging as much as possible.

Therefore, the inventors have studied a technique which provides a plurality of X-ray tubes with different irradiation angles in order to reduce the imaging time. In this configuration, the movement range of the X-ray tube is narrower than that in a case in which one X-ray tube is moved and the number of times the X-ray tube is stopped is reduced by a value corresponding to an increase in the number of X-ray tubes. Therefore, it is possible to reduce the imaging time.

However, in a case in which a plurality of X-ray tubes are provided, the arrangement interval of the X-ray tubes is limited by the size of each X-ray tube. In a case in which the arrangement interval of a plurality of X-ray tubes increases, the number of captured projection images in the unit angle is reduced. In a case in which the number of captured images is reduced, the amount of information required to reconstruct the tomographic image is reduced and the number of artifacts in the reconstructed tomographic image increases.

An object of the technology according to the present disclosure is to provide a tomosynthesis imaging apparatus that can reduce an imaging time while suppressing an artifact in a tomographic image, as compared to the related art in which tomosynthesis imaging is performed while one X-ray tube is being moved, and a method for operating the tomosynthesis imaging apparatus.

In order to achieve the object, a tomosynthesis imaging apparatus according to the present disclosure comprises: a radiation detector having an imaging surface that detects radiation transmitted through an object and captures a projection image of the object; a radiation source that has a plurality of radiation tubes which emit the radiation to the imaging surface at different irradiation angles and selectively irradiates the object with the radiation from each of the plurality of radiation tubes; and a radiation source control unit that performs movement control for moving at least one of the plurality of radiation tubes to change the radiation irradiation angle of the radiation tube with respect to the imaging surface.

Preferably, the plurality of radiation tubes are arranged in a row in the radiation source.

Preferably, in one tomosynthesis imaging operation that selectively performs the emission of the radiation from the plurality of radiation tubes to acquire a plurality of the projection images based on the emission of the radiation from each radiation tube, the radiation source control unit performs irradiation control for controlling an irradiation order of the selected radiation tubes among the plurality of radiation tubes and movement control for the selected radiation tubes among the plurality of radiation tubes.

Preferably, assuming that the irradiation angle is an angle formed between a normal line to the imaging surface which extends from a center of the imaging surface and a segment which connects the center of the imaging surface and a focus of each of the plurality of radiation tubes; the plurality of radiation tubes arranged in a row are N radiation tubes; the radiation tube disposed at one end in the arrangement direction is a first radiation tube; the radiation tube disposed at the other end is an N-th radiation tube; a segment which connects the center of the imaging surface and the focus of the first radiation tube is a first segment; a segment which connects the center of the imaging surface and the focus of the N-th radiation tube is an N-th segment; an angle formed between the first segment and the N-th segment is a spread angle W in the arrangement direction of the plurality of radiation tubes; a sum of absolute values of maximum irradiation angles in a positive direction and a negative direction from the normal line among a plurality of the irradiation angles corresponding to the plurality of projection images acquired in the one tomosynthesis imaging operation is a scanning angle KA of the radiation source required for the one tomosynthesis imaging operation; an arrangement interval of the plurality of radiation tubes is PT; and a remaining angle obtained by subtracting the spread angle W from the scanning angle KA is a difference ΔA, in a case in which KA W is satisfied, the radiation source control unit sets a movement range in a range of PT and performs the movement control. Preferably, in a case in which KA>W is satisfied, the radiation source control unit sets the movement range in a range of the larger of ΔA and PT and performs the movement control.

Preferably, in a case in which the number of the plurality of radiation tubes is N and the number of stop positions where the plurality of radiation tubes emit the radiation in the movement range is Np, the radiation source control unit is capable of directing the plurality of radiation tubes to emit the radiation a total of Mp (=N×Np) times in the one tomosynthesis imaging operation.

Preferably, the irradiation angle is the angle formed between the normal line to the imaging surface which extends from the center of the imaging surface and the segment which connects the center of the imaging surface and the focus of each of the plurality of radiation tubes, and the radiation source control unit performs control for equalizing the intervals between the focuses corresponding to the plurality of projection images acquired in the one tomosynthesis imaging operation.

Preferably, the radiation source includes a plurality of units in which the plurality of radiation tubes are divided and accommodated.

Preferably, the radiation source control unit is capable of moving each of the plurality of units in the movement control. Preferably, in the one tomosynthesis imaging operation, in a case in which at least one movement target unit to be moved among the plurality of units is moved to a next stop position for irradiation, the radiation source control unit starts to move the movement target unit while a unit other than the movement target unit is stopped for irradiation.

Preferably, a position and posture of the radiation detector are fixed during imaging.

The object is, for example, a breast.

The radiation tube includes a cathode that emits electrons and an anode that emits radiation from a focus where the electrons emitted from the cathode collide.

Preferably, the anode is a fixed anode.

Preferably, the cathode is a field emission type that emits electrons using a field emission phenomenon which occurs in a case in which an electric field is applied to a surface of a conductor.

In the radiation source, for example, the plurality of radiation tubes are linearly arranged in a plane parallel to the imaging surface.

In the radiation source, for example, the plurality of radiation tubes are arranged in a convex arc shape in which a center in the arrangement direction of the radiation tubes protrudes in a direction away from the imaging surface.

Preferably, the tomosynthesis imaging apparatus further comprises an image processing unit that reconstructs a tomographic image of the object on the basis of the plurality of projection images.

According to the present disclosure, there is provided a method for operating a tomosynthesis imaging apparatus comprising a radiation detector having an imaging surface that detects radiation transmitted through an object and captures a projection image of the object. The method comprises: a radiation source control step including irradiation control for controlling a radiation source including a plurality of radiation tubes which emit the radiation to the imaging surface at different irradiation angles such that the plurality of radiation tubes selectively irradiate the object with the radiation and movement control for moving at least one of the plurality of radiation tubes to change the radiation irradiation angle of the radiation tube with respect to the imaging surface; and an acquisition step of allowing the radiation detector to acquire a plurality of the projection images with different irradiation angles while performing the radiation source control step.

According to the technology of the present disclosure, it is possible to reduce the imaging time while suppressing an artifact in a tomographic image, as compared to the related art in which tomosynthesis imaging is performed while one X-ray tube is being moved.

BRIEF DESCRIPTION OF THE DRAWINGS

Exemplary embodiments according to the technique of the present disclosure will be described in detail based on the following figures, wherein:

FIG. 10 is a diagram illustrating an electron emission area of a cathode;

FIG. 11 is a diagram illustrating the focus of an anode;

FIG. 24 is a diagram illustrating an X-ray imaging apparatus for surgery.

DETAILED DESCRIPTION

First Embodiment

Figure 1:
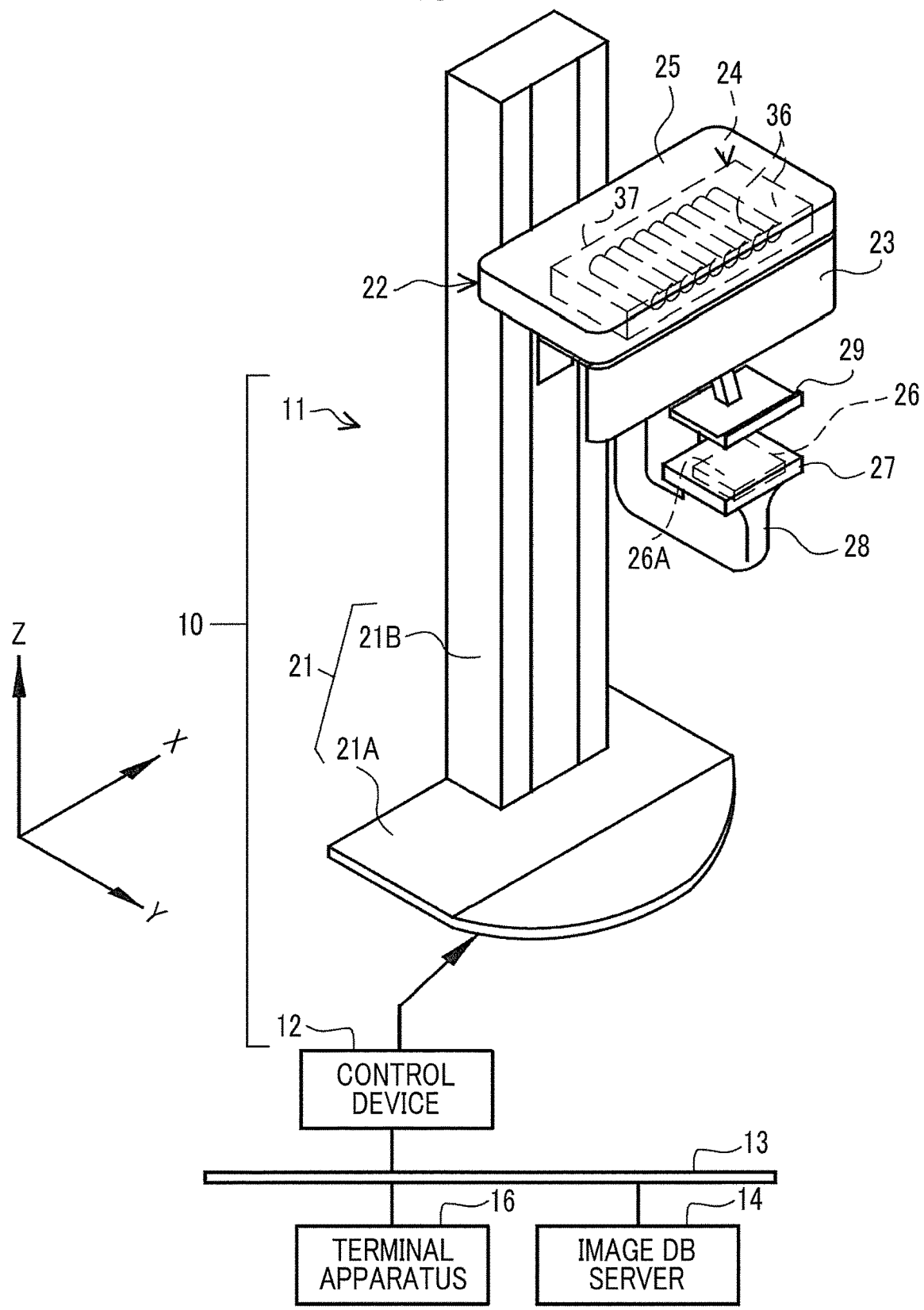
FIG. 1 is a diagram illustrating the outward appearance of a mammography apparatus.
Figure 2:
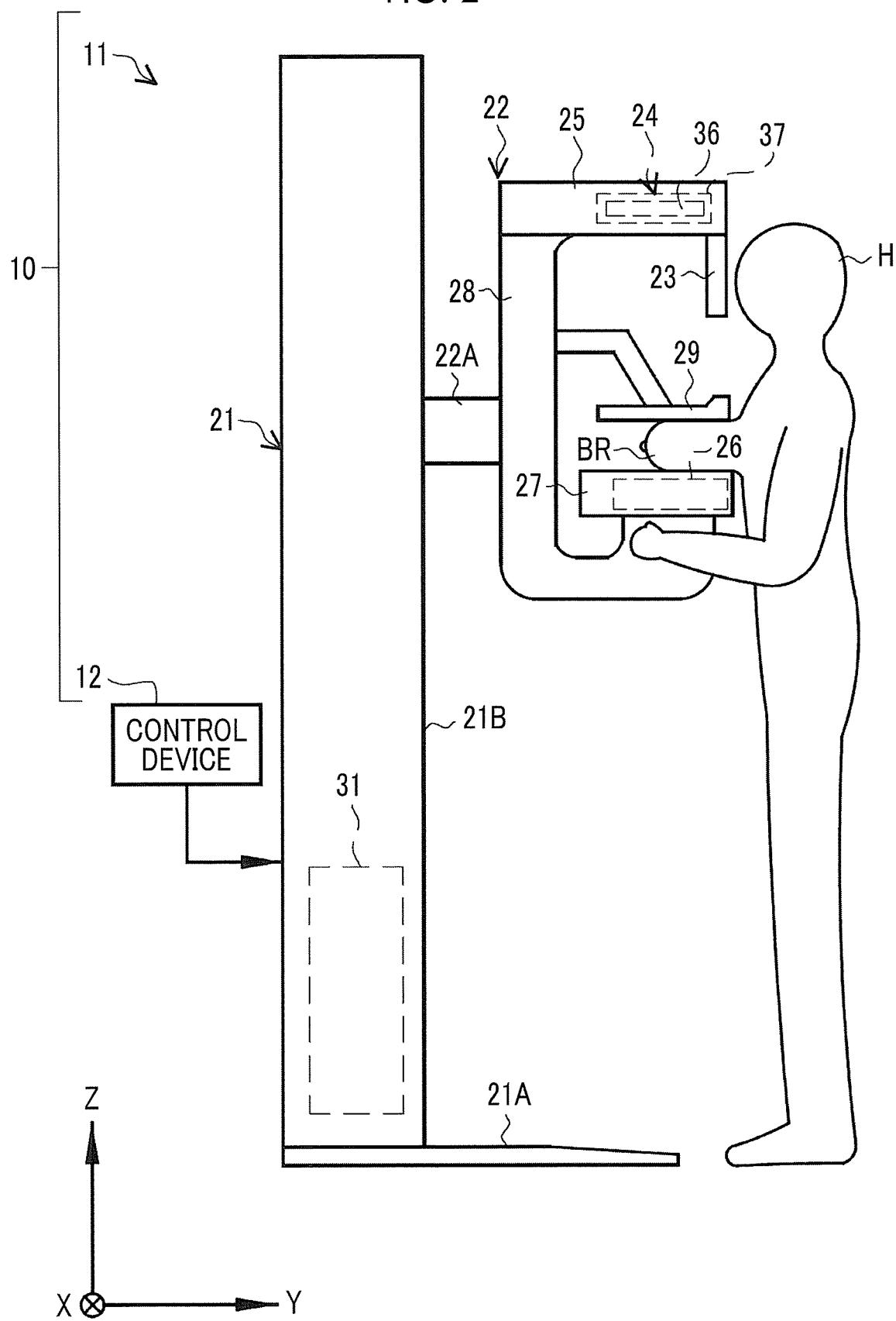
FIG. 2 is a side view illustrating the mammography apparatus.

A mammography apparatus 10 illustrated in FIGS. 1 and 2 irradiates a breast BR of a subject H which is an object with X-rays and captures an X-ray image of the breast BR. The mammography apparatus 10 has a tomosynthesis imaging function and is an example of a tomosynthesis imaging apparatus. The mammography apparatus 10 includes an apparatus main body 11 and a control device 12.

The control device 12 is connected to an image database (DB) server 14 and a terminal apparatus 16 through a network 13 so as to communicate therewith. The X-ray image captured by the mammography apparatus 10 is transmitted from the control device 12 to the image DB server 14 and is accumulated in the image DB server 14. The image DB server 14 is, for example, a picture archiving and communication system (PACS) server. The terminal apparatus 16 reads an X-ray image from the image DB server 14 and displays the X-ray image. The terminal apparatus 16 is used by, for example, a doctor to browse the X-ray image.

The apparatus main body 11 includes a stand 21 including a pedestal 21A and a support 21B that extends from the pedestal 21A in a height direction (Z direction) and a C-arm 22 which has a C-shape and is provided so as to be movable with respect to the support 21B.

The C-arm 22 comprises a radiation source accommodation portion 25 that accommodates an X-ray source 24, a detector accommodation portion 27 that accommodates an X-ray detector 26, and an arm portion 28 that integrally supports the radiation source accommodation portion 25 and the detector accommodation portion 27. In the arm portion 28, the radiation source accommodation portion 25 is provided on the upper side in the height direction (Z direction) and the detector accommodation portion 27 is provided on the lower side in the height direction at a posture facing the radiation source accommodation portion 25. The C-arm 22 is an example of an accommodation portion that accommodates the X-ray source 24 and the X-ray detector 26 at a posture where the X-ray source 24 and the X-ray detector 26 face each other.

The X-ray source 24 includes a plurality of X-ray tubes 36 and a housing 37 that accommodates the X-ray tubes 36. The X-ray source 24 is an example of a radiation source and the X-ray tube 36 is an example of a radiation tube. The X-ray source 24 selectively emits X-rays from each of the plurality of X-ray tubes 36 to the breast BR. In the radiation source accommodation portion 25, the plurality of X-ray tubes 36 are arranged in a row in the X direction. Here, one row means the arrangement state of the plurality of X-ray tubes 36 in the Z direction perpendicular to an imaging surface 26A of the X-ray detector 26, which will be described below, in a plan view.

The X-ray detector 26 detects the X-rays which have been emitted from each X-ray tube 36 and transmitted through the breast BR and outputs an X-ray image of the breast BR. The X-ray detector 26 is an example of a radiation detector.

In the C-arm 22, a compression plate 29 is provided between the radiation source accommodation portion 25 and the detector accommodation portion 27. The compression plate 29 is supported by the arm portion 28 and is movable in the Z direction. The detector accommodation portion 27 functions as an imaging table on which the breast BR is placed. The compression plate 29 is moved to the detector accommodation portion 27, on which the breast BR has been placed, in the Z direction and compresses the breast BR interposed between the compression plate 29 and the detector accommodation portion 27. The compression plate 29 is made of a material transmitting X-rays such as plastic.

The C-arm 22 is connected to the support 21B through a connection portion 22A. The C-arm 22 is movable in the Z direction by the connection portion 22A. Therefore, the height of the C-arm 22 can be adjusted according to the height of the subject H. In addition, the C-arm 22 is provided so as to be rotatable on the Y-axis, which will be described below (see FIG. 5).

A high voltage generation device 31 that generates a voltage to be applied to the X-ray source 24 is provided in the support 21B. A voltage cable (not illustrated) extending from the high voltage generation device 31 is provided in the support 21B and the connection portion 22A. One end of the voltage cable extends into the radiation source accommodation portion 25 through the support 21B and the connection portion 22A and is connected to the X-ray source 24.

Reference numeral 23 indicates a face guard. The face guard 23 is made of an X-ray shielding member and shields X-rays to protect the face of the subject H from X-rays. The face guard 23 is attached, for example, to a lower part of the radiation source accommodation portion 25. The face guard 23 may be fixed to the support 21B so as not to be rotated even in a case in which the C-arm 22 is rotated on the Y-axis.

Figure 3:
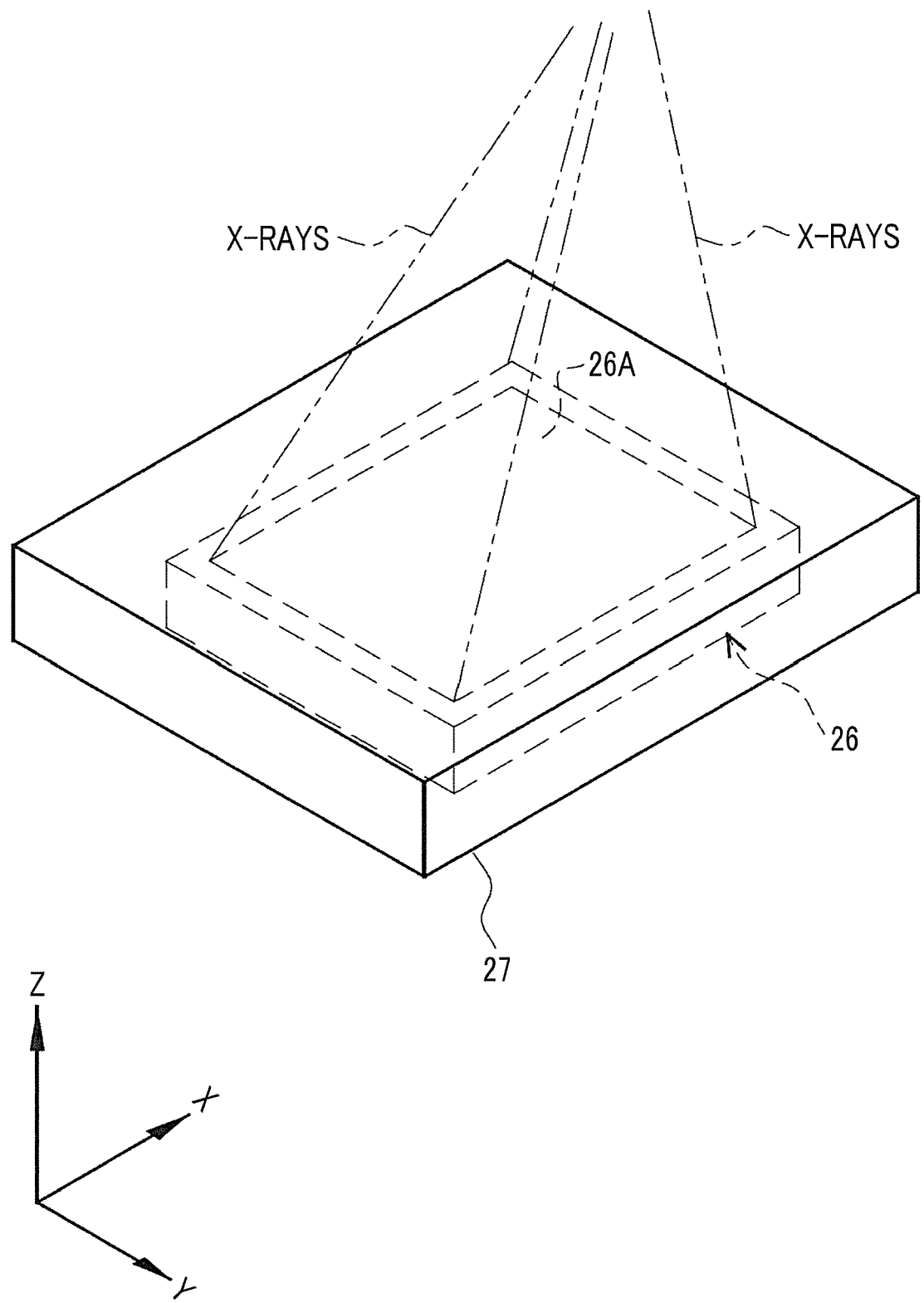
FIG. 3 is a diagram illustrating a detector accommodation portion and an X-ray detector.

As illustrated in FIG. 3, the X-ray detector 26 has an imaging surface 26A that detects the X-rays transmitted through the breast BR and captures a projection image which is an X-ray projection image of the breast BR. The imaging surface 26A is a two-dimensional plane in which pixels that convert X-rays into an electric signal are two-dimensionally arranged. The X-ray detector 26 is also referred to as a flat panel detector (FPD). The X-ray detector 26 may be an indirect conversion type that includes, for example, a scintillator converting X-rays into visible light and converts visible light emitted from the scintillator into an electric signal or a direct conversion type that directly converts X-rays into an electric signal.

In addition, for the relative position of each X-ray tube 36 with respect to the imaging surface 26A in the X direction, the center in the arrangement direction (X direction) of the X-ray tubes 36 is aligned with the center (see CP in FIG. 6) of the imaging surface 26A in the X direction. In addition, for the Y direction, in the mammography apparatus 10, the focus F (see FIG. 6) of each X-ray tube 36 is offset from the center of the imaging surface 26A in the Y direction to the front side (a side opposite to the support 21B) such that the chest wall of the breast BR is also irradiated with X-rays.

Figure 4:
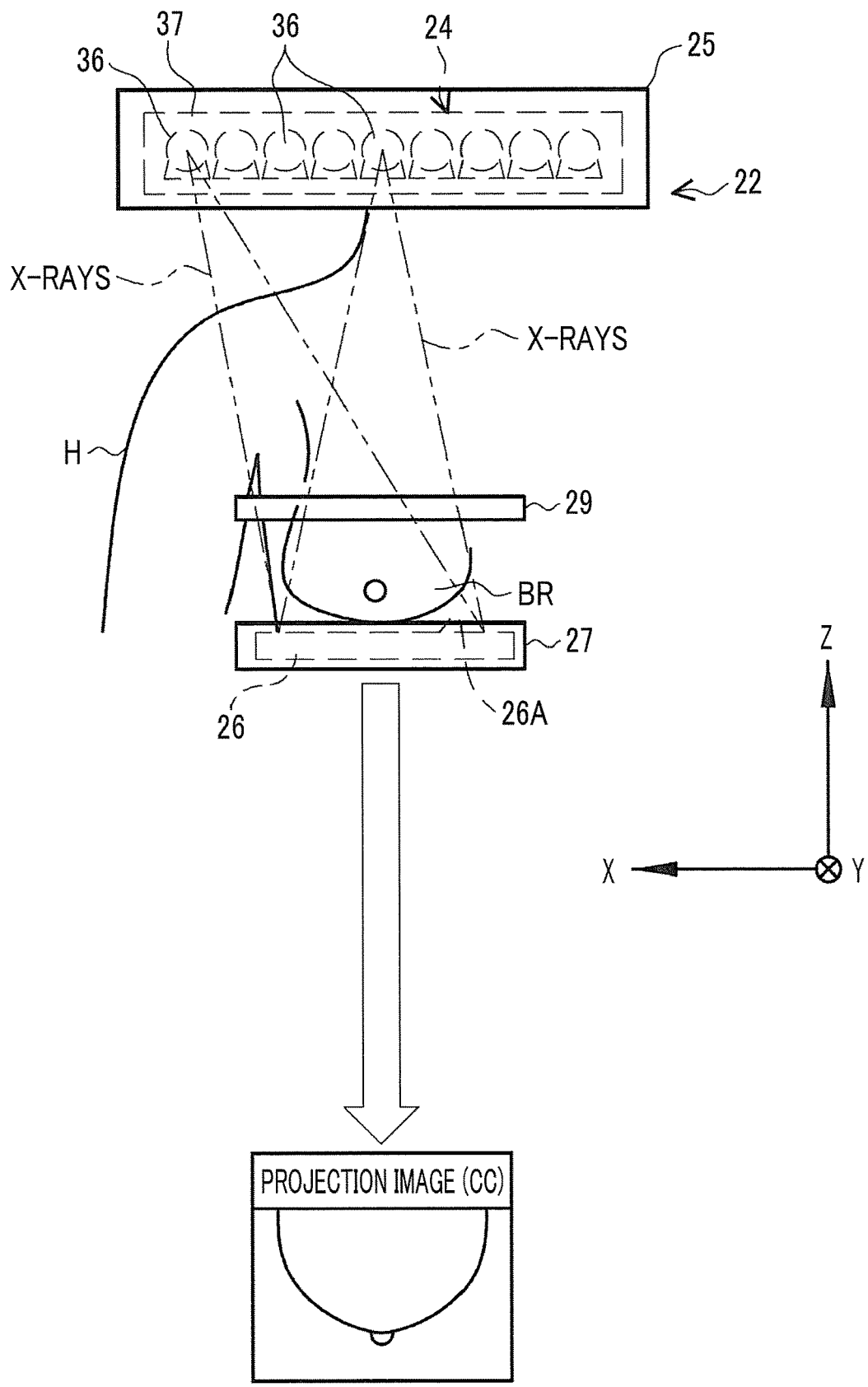
FIG. 4 is a diagram illustrating an aspect of CC imaging.
Figure 5:
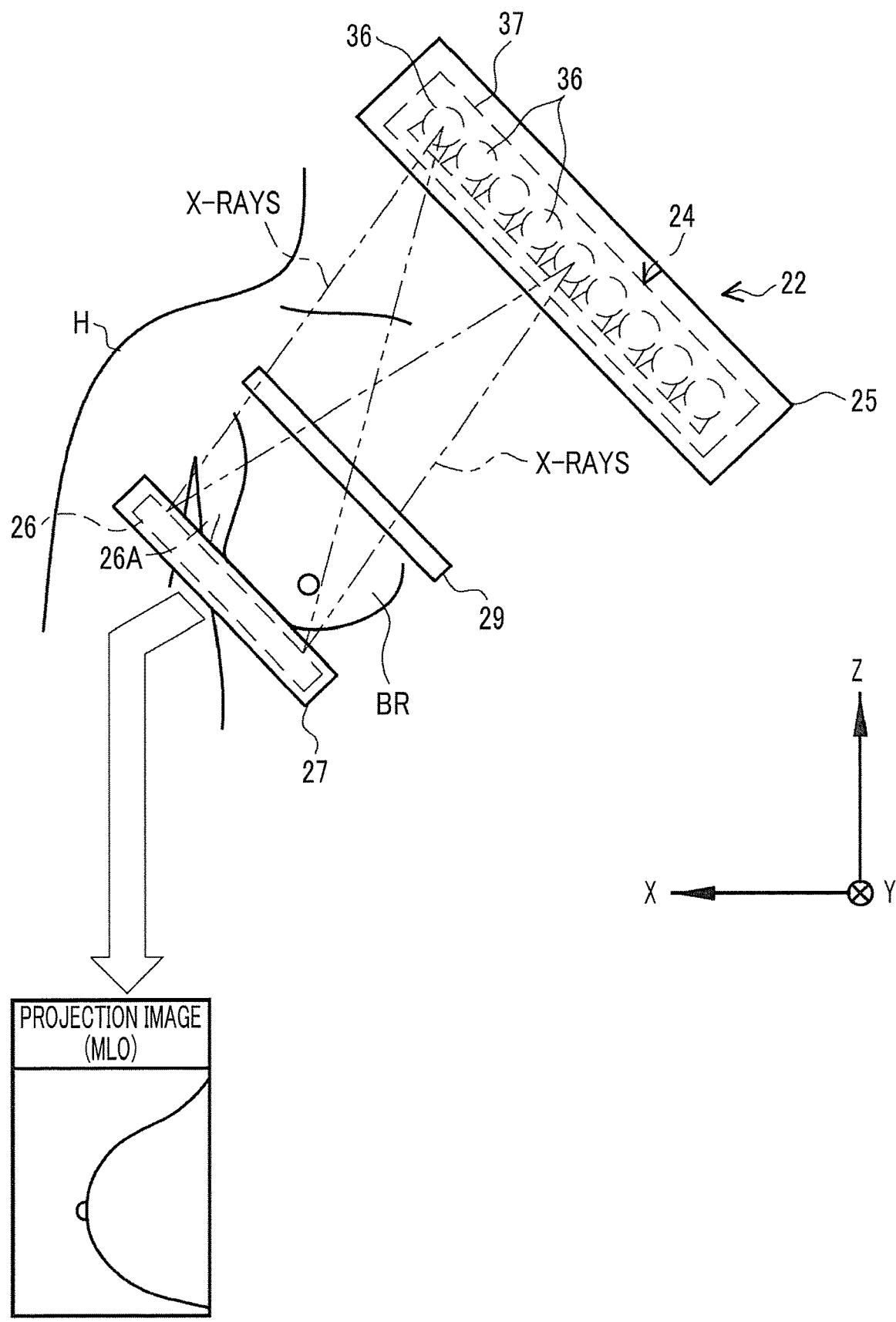
FIG. 5 is a diagram illustrating an aspect of MLO imaging.

As illustrated in FIGS. 4 and 5, the C-arm 22 is rotated on the Y-axis while the posture where the X-ray source 24 faces the imaging surface 26A of the X-ray detector 26 is maintained. Therefore, it is possible to perform imaging in two directions, such as craniocaudal view (CC) imaging illustrated in FIG. 4 and mediolateral oblique view (MLO) imaging illustrated in FIG. 5. The CC imaging is an imaging method which captures an image with the breast BR interposed in the vertical direction parallel to the Z direction and the MLO imaging is an imaging method which captures an image with the breast BR interposed in a direction that is inclined at an angle of about 60° with respect to the Z direction. In the CC imaging and the MLO imaging, a projection image (CC) and a projection image (MLO) captured in two different directions are obtained.

FIG. 4 illustrates the initial state of the C-arm 22. The imaging surface 26A is parallel to the X-Y plane. The imaging surface 26A and the X-ray source 24 face each other in the Z direction. In this example, the X direction, the Y direction, and the Z direction are used to define the imaging surface 26A and the arrangement direction of the plurality of X-ray tubes 36 in the C-arm 22. This definition is based on the premise that the C-arm 22 is in the initial state illustrated in FIG. 4. FIG. 5 illustrates a state in which the C-arm 22 is rotated on the Y-axis from the initial state. The arrangement direction of the plurality of X-ray tubes 36 is inclined with respect to the X direction. In the following description, it is premised that the C-arm 22 is in the initial state illustrated in FIG. 4.

Figure 6:
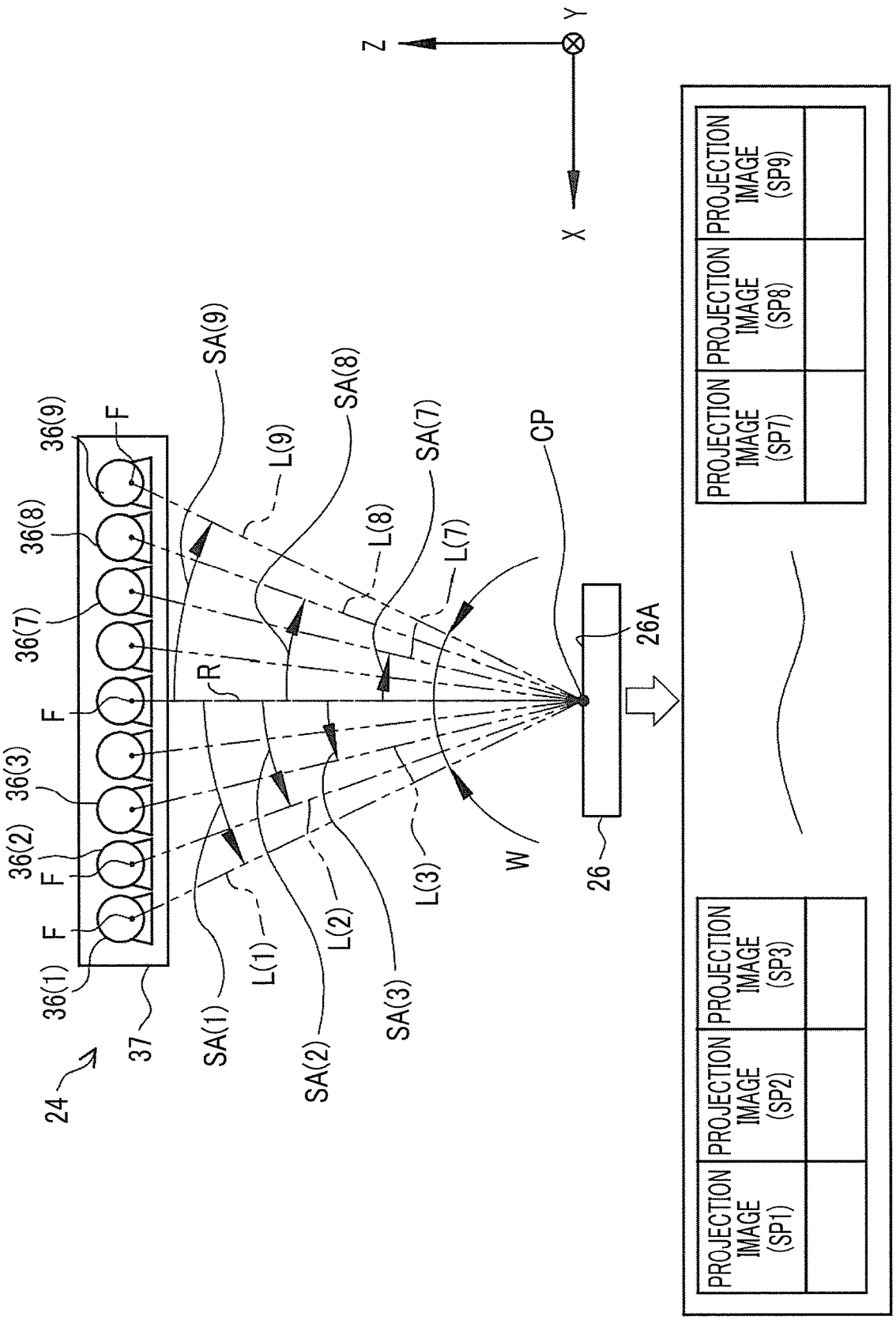
FIG. 6 is a diagram illustrating an aspect of tomosynthesis imaging.

As illustrated in FIG. 6 as an example, the X-ray source 24 includes, for example, nine X-ray tubes 36. The nine X-ray tubes 36 are linearly arranged along the X direction in the plane parallel to the imaging surface 26A. The X-ray tubes 36 are arranged at equal intervals.

The focus F of each of the nine X-ray tubes 36 is the focus at which X-rays are emitted in each X-ray tube 36 and is the irradiation position of each X-ray tube 36. Therefore, the irradiation angles SA of the nine X-ray tubes 36 with respect to the imaging surface 26A are different from each other. Here, the irradiation angle SA means an angle formed between a normal line R (also see FIG. 3) to the imaging surface 26A which extends from the center CP (also see FIG. 3) of the imaging surface 26A in the X direction and a segment L connecting the focus F which is the irradiation position of each X-ray tube 36 and the center CP in the X-Z plane.

In the tomosynthesis imaging, it is necessary to acquire a plurality of projection images SP with different X-ray irradiation angles SA. Since the mammography apparatus 10 includes the plurality of X-ray tubes 36 with different irradiation angles SA, the mammography apparatus 10 can acquire the projection images SP with different irradiation angles SA even in a state in which the plurality of X-ray tubes 36 are fixed.

In FIG. 6, in order to distinguish, for example, the X-ray tubes 36 and the irradiation angles SA of the X-ray tubes 36, parenthesized numbers (1) to (9) are given such that an X-ray tube 36 disposed at the left end which is one end in the arrangement direction is the first X-ray tube 36 and an X-ray tube 36 disposed at the other end is the ninth X-ray tube 36. The irradiation angle SA(1) of the X-ray tube 36(1) disposed at the left end is an angle formed between the normal line R and a segment L(1) connecting the focus F of the X-ray tube 36(1) and the center CP of the imaging surface 26A. The irradiation angle SA(2) of the second X-ray tube 36(2) from the left side is an angle formed between the normal line R and a segment L(2) connecting the focus F of the X-ray tube 36(2) and the center CP of the imaging surface 26A. The irradiation angle SA(1) of the first X-ray tube 36(1) is larger than the irradiation angle SA(2) of the second X-ray tube 36(2).

Similarly, the irradiation angle SA(9) of the X-ray tube 36(9) disposed at the right end is an angle formed between the normal line R and a segment L(9) connecting the focus F of the X-ray tube 36(9) and the center CP of the imaging surface 26A. The irradiation angle SA(8) of the second X-ray tube 36(8) from the right side is an angle formed between the normal line R and a segment L(8) connecting the focus F of the X-ray tube 36(8) and the center CP of the imaging surface 26A. The irradiation angle SA(9) of the ninth X-ray tube 36(9) is larger than the irradiation angle SA(8) of the eighth X-ray tube 36(8). In a case in which the X-ray tubes 36 are linearly arranged along the X direction in the plane parallel to the imaging surface 26A as in this example, as the position of each X-ray tube 36 becomes further away from the center CP, the irradiation angle SA of the X-ray tube 36 becomes larger.

In addition, reference numeral W indicates an angle formed between the segments L corresponding to the X-ray tubes 36 at both ends in the X-ray source 24 and means a spread angle in the arrangement direction (X direction) of the plurality of X-ray tubes 36 in the X-ray source 24. In this example, the spread angle W is the angle formed between the segment L(1) corresponding to the X-ray tube 36(1) at the left end and the segment L(9) corresponding to the X-ray tube 36(9) at the right end.

One tomosynthesis imaging operation of the mammography apparatus 10 means an operation of selectively emitting X-rays from the plurality of X-ray tubes 36 and acquiring a plurality of projection images SP based on the emission of the X-rays from each selected X-ray tube 36. The plurality of projection images SP have different irradiation angles SA. FIG. 6 illustrates an aspect in which nine projection images SP, that is, projection images SP1 to SP9 are acquired.

Figure 7:
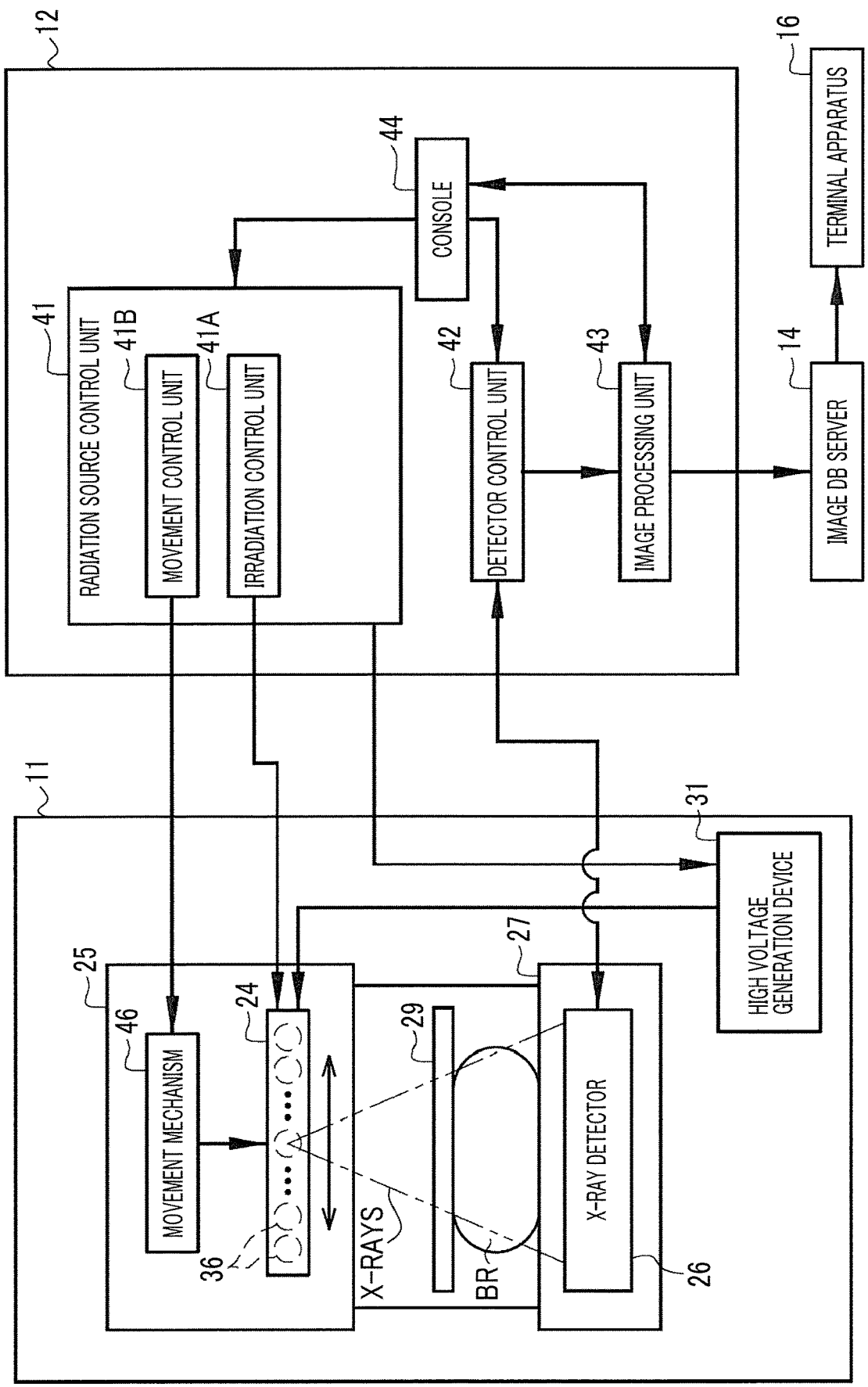
FIG. 7 is a block diagram schematically illustrating an electrical configuration of the mammography apparatus.

As illustrated in FIG. 7, the control device 12 controls each unit of the apparatus main body 11. The control device 12 comprises a radiation source control unit 41, a detector control unit 42, an image processing unit 43, and a console 44.

The radiation source control unit 41 comprises an irradiation control unit 41A and a movement control unit 41B. The irradiation control unit 41A controls the irradiation conditions of the X-ray source 24 and the irradiation timing and irradiation order of each X-ray tube 36. For example, the irradiation conditions include the tube voltage, tube current, and irradiation time of the X-ray tube 36 and are set according to the size of the breast BR and the purpose of imaging. The tube voltage defines the energy of X-rays, and the tube current and the irradiation time define the cumulative amount of X-rays. The tube voltage is set through the high voltage generation device 31.

The movement control unit 41B controls the movement of the X-ray source 24 through a movement mechanism 46. In this example, the X-ray source 24 can be moved in a direction (X direction) parallel to the imaging surface 26A. The movement mechanism 46 is provided in the radiation source accommodation portion 25 and includes, for example, a rack-and-pinion sliding mechanism and a motor for driving the sliding mechanism. The movement control unit 41B controls the movement timing and amount of movement of the X-ray source 24 through the movement mechanism 46.

The detector control unit 42 performs synchronization control which directs the X-ray detector 26 to start an imaging operation in synchronization with the start timing of a preparation operation, such as a reset process of the X-ray detector 26, and the irradiation timing of the X-ray source 24. In addition, the detector control unit 42 acquires the projection image SP from the X-ray detector 26.

The image processing unit 43 performs image processing, such as frequency processing, a noise filtering process, and a dynamic range adjustment process, for the projection image SP acquired from the detector control unit 42. The image processing unit 43 reconstructs a tomographic image including a structure of any tomographic plane of the breast BR on the basis of a plurality of projection images SP with different irradiation angles SA, in addition to the above-mentioned general image processing.

Figure 8:
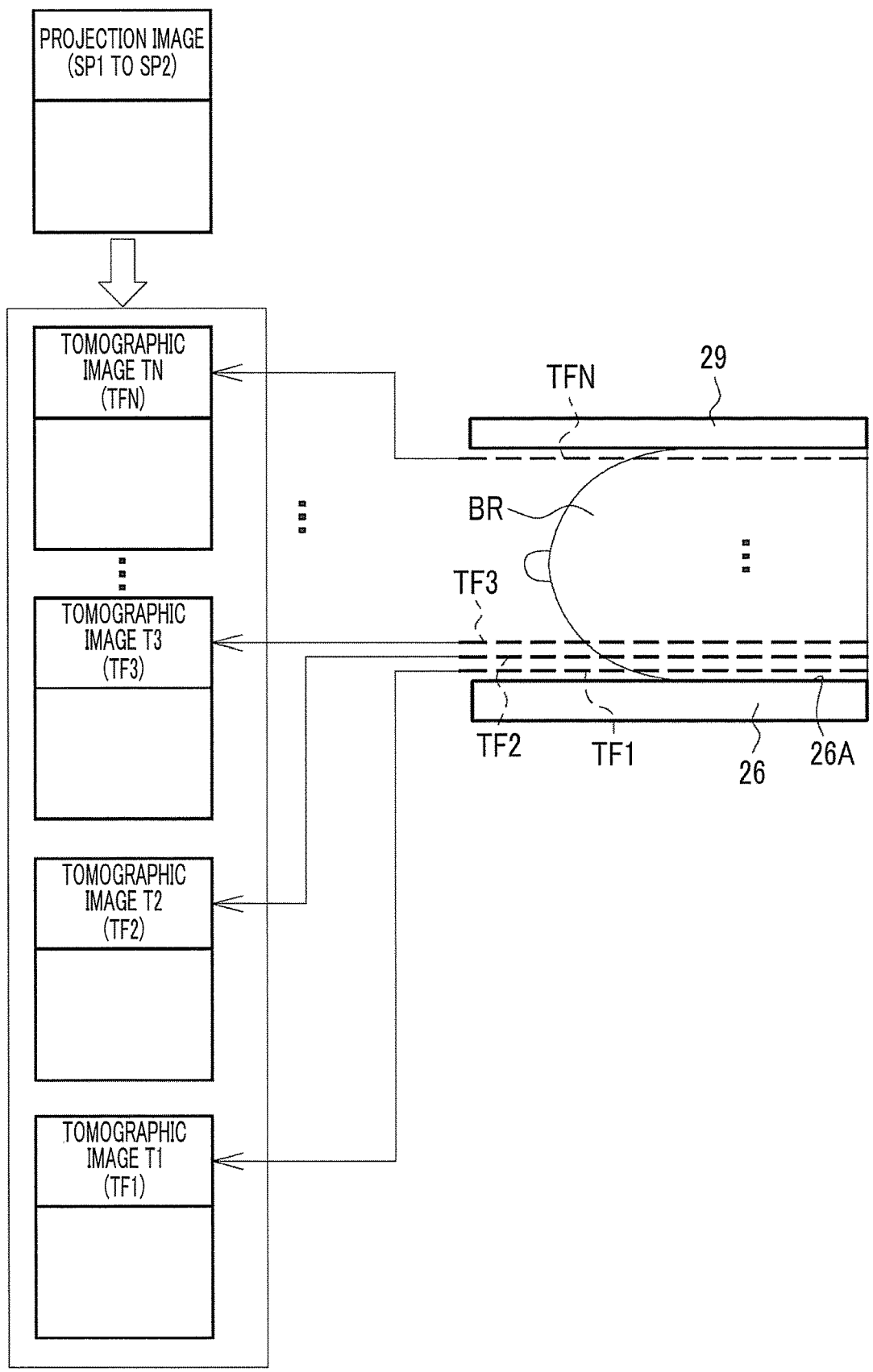
FIG. 8 is a diagram illustrating a tomographic image.

As illustrated in FIG. 8, the image processing unit 43 generates tomographic images T1 to TN corresponding to any tomographic planes TF1 to TFN of the breast BR from the plurality of projection images SP, using a known method such as a filtered back projection (FBP) method or a shift-and-add method. The tomographic plane TF is a plane parallel to the imaging surface 26A of the X-ray detector 26. In the tomographic images T1 to TN, images in which structures in the tomographic planes TF1 to TFN of the breast BR have been highlighted are obtained.

In FIG. 7, the console 44 is an operation terminal that is used by a medical staff, such as a radiology technical or a doctor, to operate the mammography apparatus 10. The console 44 has an imaging condition setting function and a function of displaying the X-ray image acquired by the X-ray detector 26 on a display such that the X-ray image is checked. The imaging conditions include, for example, the scanning angle KA (see, for example, FIG. 12) in a case in which tomosynthesis imaging is performed in addition to the irradiation conditions of the X-ray source 24.

Here, the scanning angle KA means the sum of the absolute values of the maximum irradiation angles SA in the positive direction (clockwise direction) and the negative direction (counterclockwise direction) from the normal line R among a plurality of irradiation angles SA corresponding to a plurality of projection images SP acquired by one tomosynthesis imaging operation.

That is, in a case in which the X-ray source 24 is not moved in the X direction, the spread angle W illustrated in FIG. 6 is the maximum value of the scanning angle KA. The scanning angle KA may be set to be smaller than the spread angle W illustrated in FIG. 6 or may be set to be larger than the spread angle W by movement control for the X-ray source 24. As the scanning angle KA becomes larger, a projection image SP with a larger irradiation angle SA is obtained. As the scanning angle KA becomes larger, depth resolution becomes higher. Therefore, it is possible to create a tomographic image in which the overlap or lesion structure of the mammary glands is clearly separated. In addition, since the irradiation angle SA of X-rays becomes smaller as the scanning angle KA becomes smaller, a region that can be captured as an image in the entire breast BR is large. The scanning angle KA is set according to the purpose of imaging. The scanning angle KA is set in the range of, for example, 15° to 60°.

Figure 9:
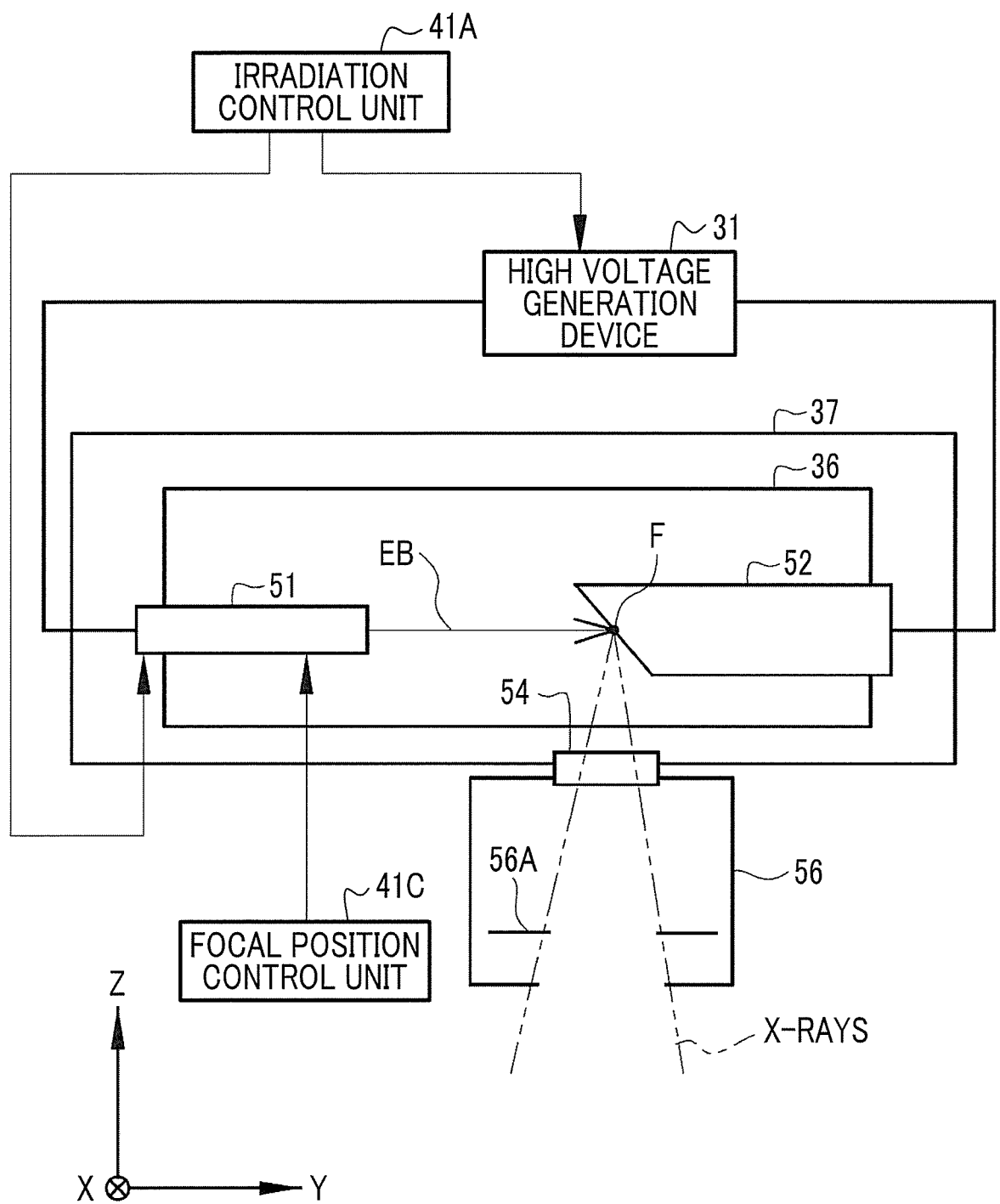
FIG. 9 is a diagram illustrating a configuration of an X-ray tube.

As illustrated in FIG. 9, the X-ray tube 36 comprises a cathode 51 and an anode 52. The cathode 51 and the anode 52 are accommodated in a vacuum glass container with a substantially cylindrical shape. The cathode 51 is an electron emission source that emits electrons EB to the anode 52. The anode 52 is a target with which the electrons EB emitted from the cathode 51 collide. For example, tungsten or molybdenum is used as the material forming the anode 52. The X-ray tube 36 according to this example is a fixed anode type in which a fixed anode is used as the anode 52. The fixed anode means a type without a rotating structure for rotating a disk-shaped anode, unlike a rotating anode type.

The cathode 51 and the anode 52 are electrically connected to the high voltage generation device 31. The irradiation control unit 41A controls the high voltage generation device 31 such that a high voltage is applied between the cathode 51 and the anode 52. The cathode 51 according to this example is a cold cathode type which will be described below. The irradiation control unit 41A and the cathode 51 are connected by a control signal line. The irradiation control unit 41A controls a gate voltage applied to a gate electrode 51B, which will be described below, through the control signal line in a state in which a high voltage is applied between the cathode 51 and the anode 52. The emission of the electrons EB from the cathode 51 is controlled by the control of the gate voltage. In a case in which the electrons EB emitted from the cathode 51 collide with the anode 52, X-rays are emitted from the focus F where the electrons EB have collided.

The X-ray tube 36 is accommodated in the housing 37 filled with insulating oil. The housing 37 is provided with an X-ray transmission window 54. The X-ray transmission window 54 is made of a material transmitting X-rays and emits X-rays to the outside of the housing 37 while sealing the inside of the housing 37. An irradiation field limiter 56 (also referred to as a collimator) which limits the irradiation field of X-rays in the breast BR is provided on the front surface of the X-ray transmission window 54. The X-rays emitted from the X-ray transmission window 54 are incident on the irradiation field limiter 56. The irradiation field limiter 56 includes a plurality of shielding plates 56A that shield X-rays. The plurality of shielding plates 56A define, for example, a rectangular irradiation opening. The plurality of shielding plates 56A are moved to adjust the size of the irradiation opening.

As illustrated in FIG. 10, the cathode 51 according to this example is a cold cathode type, specifically, a field emission type which emits electrons using a field emission phenomenon that occurs in a case in which the electric field is applied to the surface of a conductor. The diameter of the X-ray tube 36 is, for example, equal to or less than about 50 mm.

The cathode 51 of the field emission type has, for example, a structure in which an emitter electrode 51A and a gate electrode 51B are provided on a semiconductor substrate 51C made of crystalline silicon. The emitter electrode 51A is obtained by, for example, forming a carbon nanotube in a conical shape. The emitter electrode 51A functions as an electron emission area which emits the electrons EB.

The gate electrode 51B is connected to the emitter electrode 51A. As described above, in a case in which X-rays are emitted, the irradiation control unit 41A controls the high voltage generation device 31 such that a high voltage is applied between the cathode 51 and the anode 52. In this state, the irradiation control unit 41A applies a gate voltage to the gate electrode 51B. In a case in which the gate voltage is applied to the gate electrode 51B, the electrons EB are emitted from the emitter electrode 51A connected to the gate electrode 51B.

In addition, a focusing electrode 51D is provided around the emitter electrode 51A. In a case in which a focusing voltage is applied to the focusing electrode, the electrons EB emitted from the emitter electrode 51A are accelerated toward the anode 52 and a beam of the electrons EB is focused.

As in this example in which the X-ray tubes 36 are linearly arranged in the plane parallel to the imaging surface 26A, even in a case in which the arrangement interval PT of the X-ray tubes 36 is equal, the difference between the irradiation angles SA of the adjacent X-ray tubes 36 is not the same and the interval between the irradiation angles SA is not equal, unlike a case in which the X-ray tubes 36 are arranged in an arc shape (see FIG. 18), which will be described below. Specifically, in FIG. 12, in a case in which PA indicating the difference between the irradiation angle SA(8) of the X-ray tube 36(8) and the irradiation angle SA(9) of the X-ray tube 36(9) is an angle PA corresponding to the arrangement interval PT, the angle PA corresponding to the arrangement interval PT is the maximum in the vicinity of the center and is gradually reduced toward both ends. As such, in the configuration in which a plurality of X-ray tubes 36 are linearly arranged, even in a case in which the arrangement interval PT of the X-ray tubes 36 is equal, the angle PA corresponding to the arrangement interval PT is gradually reduced from the vicinity of the center to both ends. However, in a case in which the arrangement interval PT is equal, the change rate of the angle PA is regular.

Figure 13:
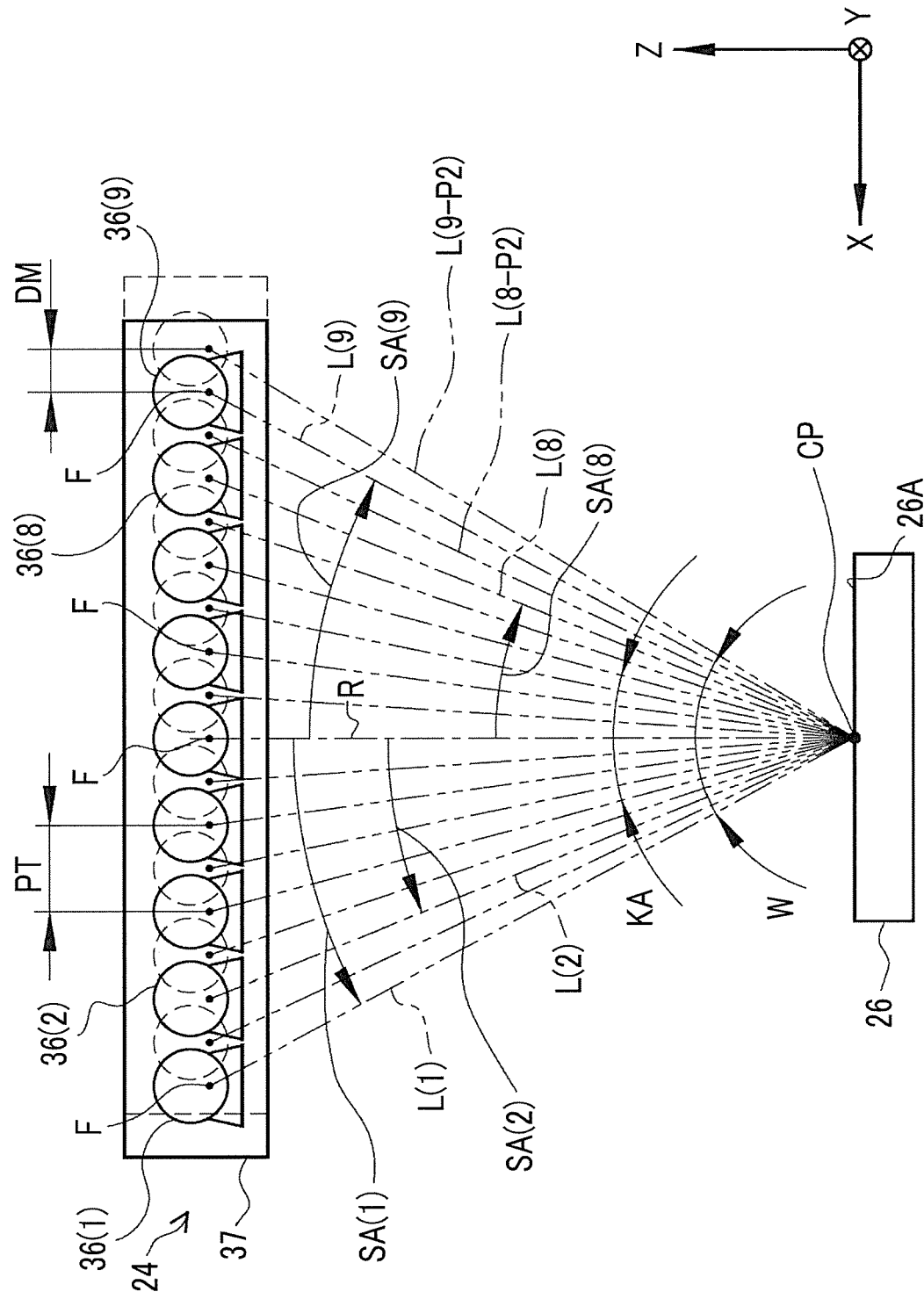
FIG. 13 is a diagram illustrating an aspect in which the plurality of X-ray tubes are moved in an arrangement direction.

As illustrated in FIG. 13, the movement control unit 41B of the radiation source control unit 41 performs movement control for moving the plurality of X-ray tubes 36 along the arrangement direction (X direction) in order to change the irradiation angles SA of the plurality of X-ray tubes 36. In this example, since the plurality of X-ray tubes 36 are accommodated in one housing 37, the movement control unit 41B integrally moves all of the plurality of X-ray tubes 36.

X-rays are emitted in a state in which the plurality of X-ray tubes 36 are stopped at a predetermined stop position. The radiation source control unit 41 moves the plurality of X-ray tubes 36 to the stop position and directs the plurality of X-ray tubes 36 to selectively emit radiation at the stop position to perform imaging. Then, the radiation source control unit 41 moves the plurality of X-ray tubes 36 to the next stop position and directs the plurality of X-ray tubes 36 to selectively emit radiation at the stop position to perform imaging. In one tomosynthesis imaging operation, the movement, the stop, and the irradiation are repeated.

The stop position and movement pitch of the plurality of X-ray tubes 36 and the movement range of the plurality of X-ray tubes 36 in one tomosynthesis imaging operation are predetermined. The movement pitch is the interval between the stop positions. The movement range is the sum of the amounts of movement of the plurality of X-ray tubes 36 in one tomosynthesis imaging operation.

The arrangement interval PT of the X-ray tubes 36 occurs in the X-ray source 24 and the arrangement interval PT is limited by, for example, the diameter of the X-ray tube 36. Therefore, there is a limit in reducing the arrangement interval PT. The plurality of X-ray tubes 36 need to be moved to set the irradiation position in the range of the arrangement interval PT.

Therefore, it is possible to set the irradiation position in the range of the arrangement interval PT by setting the movement pitch to be less than the arrangement interval PT. As a result, the number of irradiation positions in the scanning angle KA increases. As the number of stop positions becomes larger due to a reduction in the movement pitch, the density of the irradiation positions in the scanning angle KA becomes higher.

For example, in a case in which the plurality of X-ray tubes 36 are moved from a position represented by a solid line to a position represented by a dashed line in FIG. 13, the segment L(8) corresponding to the focus F of the X-ray tube 36(8) is changed to a segment L(8-P2) and the segment L(9) corresponding to the focus F of the X-ray tube 36(9) is changed to a segment L(9-P2). This holds for the other X-ray tubes 36. Therefore, the plurality of X-ray tubes 36 are moved to set the irradiation position in the range of the arrangement interval PT. The density of the irradiation positions in the scanning angle KA increases.

Figure 12:
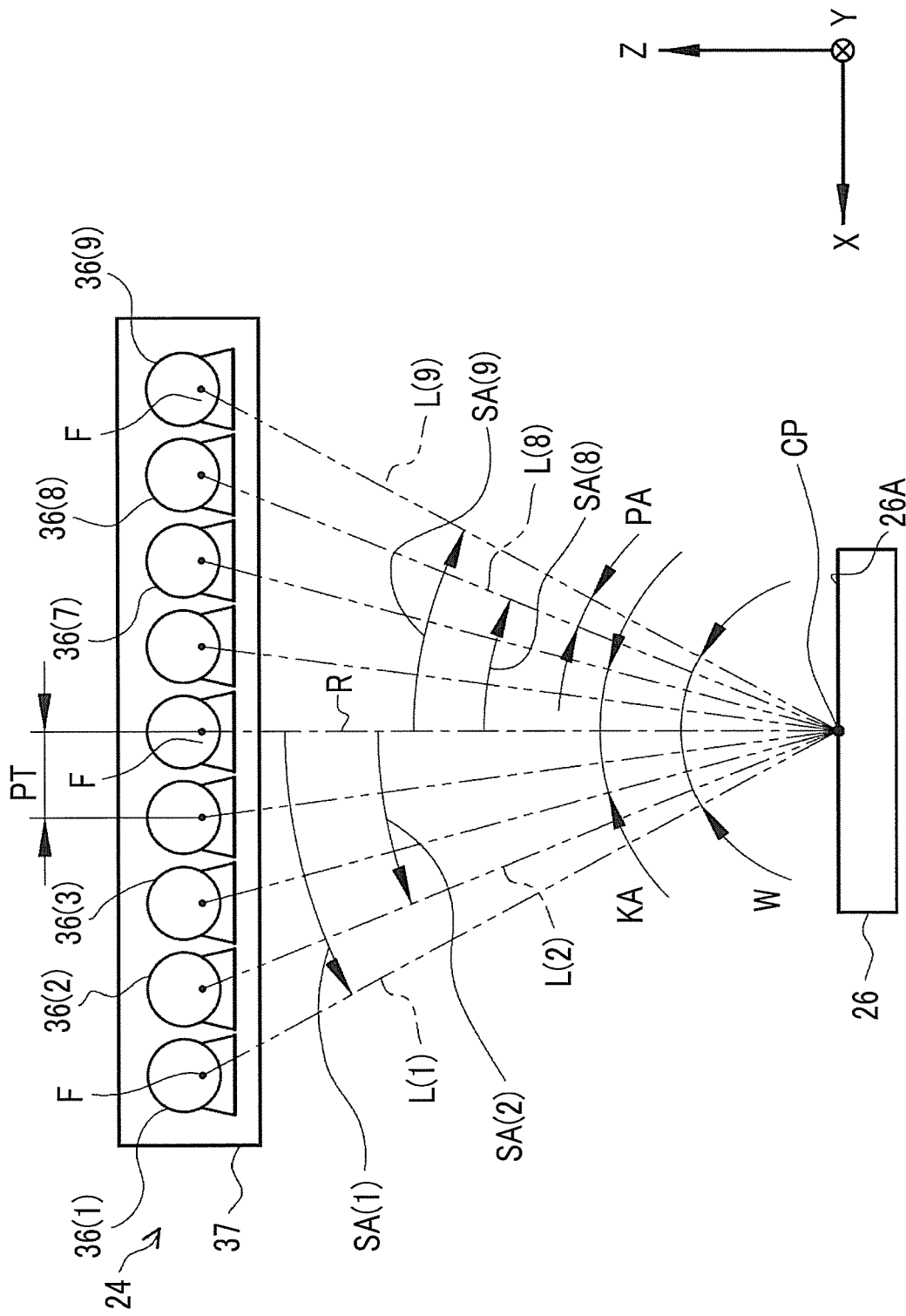
FIG. 12 is a diagram illustrating the irradiation positions of a plurality of X-ray tubes.

As illustrated in FIG. 12, in a case in which the scanning angle KA is equal to or less than the spread angle W (in the case of KA≤W), the movement range is set in the range of the arrangement interval PT of the X-ray tubes 36. The reason is as follows. In a case in which the scanning angle KA is equal to or less than the spread angle W and the plurality of X-ray tubes 36 are moved by a distance corresponding to the arrangement interval PT, each X-ray tube 36 is only shifted to the position of an adjacent X-ray tube 36 and the further movement of the X-ray tube 36 does not contribute to increasing the density of the irradiation positions at all.

The movement control unit 41B performs movement control in the set movement range according to a predetermined movement pitch and a predetermined number of stop positions. This movement control makes it possible for the radiation source control unit 41 to direct the X-ray tubes 36 to emit X-rays a maximum of the following number of times in one tomosynthesis imaging operation. That is, in a case in which the number of X-ray tubes 36 is N and the number of stop positions where the plurality of X-ray tubes 36 emit radiation in the movement range is Np, the radiation source control unit 41 can direct the plurality of X-ray tubes 36 to emit radiation a total of Mp (=N×Np) times in one tomosynthesis imaging operation.

Therefore, in a case in which the above-mentioned movement control is performed, the X-ray detector 26 can acquire a maximum of Mp projection images SP with different irradiation angles SA in one tomosynthesis imaging operation. In a case in which all of the nine X-ray tubes 36 are used and two stop positions are set as in this example, Mp=N×Np=9×2=18 is established and a total of 18 projection images SP with different irradiation angles SA are acquired.

In a case in which the above-mentioned movement control is performed, the movement control unit 41B performs control for equalizing the intervals of the focuses F corresponding to a plurality of projection images SP acquired in one tomosynthesis imaging operation. For example, this control is performed as follows.

In FIG. 13, it is assumed that a position represented by a solid line is a first stop position and a position represented by a dashed line is a second stop position in the X-ray source 24. The first stop position is the same position as that illustrated in FIG. 12 and the second stop position is a position moved by a predetermined movement distance DM from the first stop position in the X direction.

In this example, the X-ray tubes 36 are arranged at equal intervals and the arrangement interval PT of the X-ray tubes 36 is equal. The movement distance DM is set to half of the arrangement interval PT. In this case, at the first stop position represented by the solid line and the second stop position represented by the dashed line, the focuses F of all of the X-ray tubes 36 do not overlap each other.

In addition, the X-ray tube 36 at the second stop position is disposed at an intermediate position of the arrangement interval PT between the X-ray tubes 36 at the first stop position. On the linear movement trajectory of each focus F, the focuses F at the first stop position and the focuses F at the second stop position are mixed, and the interval between all of the focuses F is half of the arrangement interval PT and is equal. Here, it is assumed that the range of equality includes an error of ±5% in addition to perfect equality.

Figure 14:
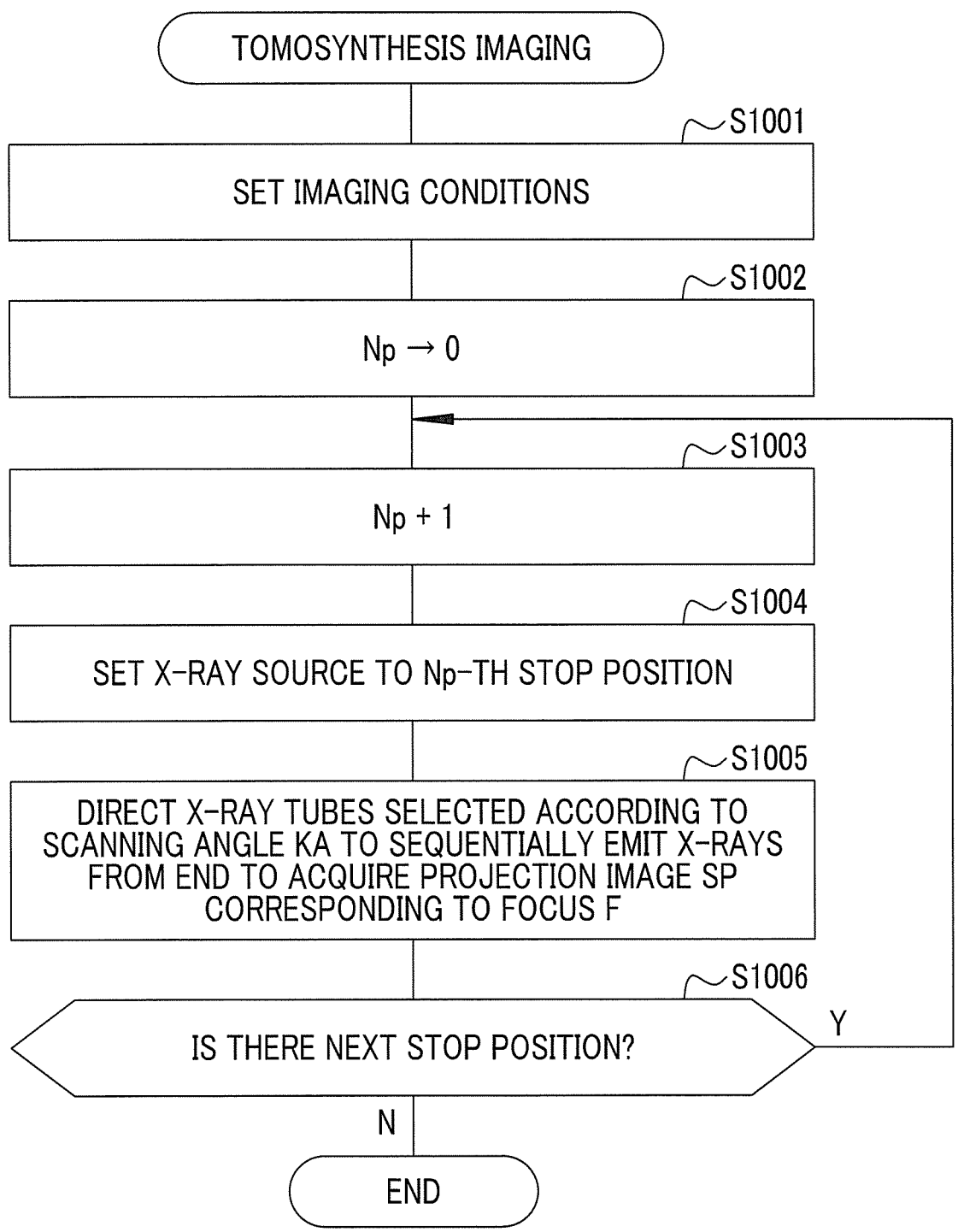
FIG. 14 is a flowchart illustrating the procedure of a tomosynthesis imaging process.

Next, the operation of the above-mentioned structure will be described with reference to a flowchart illustrated in FIG. 14. In a case in which the mammography apparatus 10 performs tomosynthesis imaging, in Step S1001, imaging conditions are set to the mammography apparatus 10 through the console 44. The imaging conditions include, for example, X-ray irradiation conditions, the scanning angle KA, a stop position, and a movement pitch. The irradiation conditions are set according to, for example, the thickness of an object. In addition, for example, an appropriate combination of the scanning angle KA, the stop position, and the movement pitch is registered as an imaging menu in advance. In this case, the imaging conditions are set by selecting the imaging menu.

Then, the breast BR of the subject H is placed on the detector accommodation portion 27 that functions as an imaging table. Then, the breast BR is compressed by the compression plate 29 and is positioned. Then, in a case in which an operation command to start imaging is input through the console 44, tomosynthesis imaging starts.

In Step S1002, the movement control unit 41B sets "0" to the number of stop positions Np in a counter that counts the number of stop positions set as the imaging conditions to perform initialization. Then, in Step S1003, the movement control unit 41B increments the number of stop positions Np by "1".

In Step S1004, the movement control unit 41B moves the X-ray source 24 (a plurality of X-ray tubes 36) to an Np-th stop position and sets the X-ray source 24 to the stop position.

In Step S1005, the irradiation control unit 41A directs the X-ray tubes 36 selected according to the scanning angle KA to sequentially emit X-rays, starting from the first X-ray tube 36 from the left end toward the right end. Then, the X-ray detector 26 acquires a plurality of projection images SP of the breast BR corresponding to the focuses F of each of the X-ray tubes 36.

In Step S1006, the movement control unit 41B determines whether there is the next stop position. In a case in which there is the next stop position (Y in Step S1006), the process returns to Step S1003. The number of stop positions Np is incremented by "1" and the process up to Step S1005 is repeated. For example, at the next stop position, the irradiation control unit 41A directs a plurality of X-ray tubes 36 to emit X-rays in the same order as that at the previous stop position.

In a case in which the number of stop positions Np reaches a predetermined value Np in Step S1006, the movement control unit 41B determines that there is no next stop position (N in Step S1006). Then, the mammography apparatus 10 ends one tomosynthesis imaging operation.

The example in which tomosynthesis imaging is performed using the mammography apparatus 10 has been described. However, the mammography apparatus 10 can perform simple X-ray imaging in addition to the tomosynthesis imaging. The simple X-ray imaging means imaging which irradiates the breast BR with X-rays from the irradiation position where the irradiation angle SA of X-rays is approximately zero to obtain the projection image SP. The mammography apparatus 10 includes a plurality of X-ray tubes 36. In the mammography apparatus 10, for example, one X-ray tube 36 located at the center in the arrangement direction of the X-ray tubes 36, for example, one central X-ray tube 36(5) which is the fifth X-ray tube 36 from the end in the example illustrated in FIG. 12 is selected and the simple X-ray imaging is performed. In addition, instead of the simple X-ray imaging, an image combination process may be performed on the basis of a plurality of projection images SP acquired by the tomosynthesis imaging to generate a composite two-dimensional image equivalent to the image obtained by the simple X-ray imaging.

As described in detail above, the mammography apparatus 10 according to this example includes a plurality of X-ray tubes 36 and the irradiation angles SA of the X-ray tubes 36 with respect to the imaging surface 26A are different from each other since the irradiation positions of the X-ray tubes 36 are different from each other. Therefore, the amount of movement of the X-ray tubes required to acquire the projection images SP at a plurality of irradiation angles SA is less than that in the related art in which tomosynthesis imaging is performed by changing the irradiation position while moving one X-ray tube. Therefore, it is possible to reduce the imaging time in one tomosynthesis imaging operation.

The movement control unit 41B of the radiation source control unit 41 performs movement control for moving the plurality of X-ray tubes 36 in order to change the irradiation angles SA of the plurality of X-ray tubes 36. The movement of the X-ray tubes 36 makes it possible to set the irradiation positions at an interval shorter than the arrangement interval PT of each X-ray tube 36. Therefore, it is possible to increase the number of irradiation positions in the range of the scanning angle KA and to suppress a reduction in the number of projection images SP captured in the range of the scanning angle KA, as compared to a case in which the movement control is not performed. In a case in which the number of projection images SP captured in the range of the scanning angle KA is increased, artifacts (noise) in the reconstructed tomographic image are suppressed.

In addition, the plurality of X-ray tubes 36 are arranged in a row. Therefore, even in a case in which the movement control is performed, all of the focuses F of the plurality of X-ray tubes 36 at a plurality of stop positions are arranged in a row. As a result, since the same tomographic image reconstruction calculation as that in the related art in which one X-ray tube 36 is moved in one direction is performed, the calculation process is simplified.

In the radiation source control unit 41, the irradiation control unit 41A performs irradiation control for controlling the irradiation order of the X-ray tubes 36 selected from the plurality of X-ray tubes 36 and the movement control unit 41B performs movement control for the X-ray tubes 36 selected from the plurality of X-ray tubes 36. The control of the irradiation order makes it possible to perform appropriate control corresponding to various demands.

In the above-mentioned example, the radiation source control unit 41 performs the following control as a combination of the irradiation order control and the movement control. The irradiation control unit 41A directs a plurality of selected X-ray tubes 36 to emit X-rays a plurality of number of times at two positions, that is, the first stop position and the second stop position. The irradiation control unit 41A directs a plurality of X-ray tubes 36 to emit X-rays in the same irradiation order at each stop position. Therefore, the irradiation intervals are the same in a plurality of irradiation operations of each X-ray tube 36 in one tomosynthesis imaging operation. As a result, a variation in the deterioration of each X-ray tube 36 caused by a difference in the irradiation interval is prevented.

In one tomosynthesis imaging operation, in a case in which the scanning angle KA is equal to or less than the spread angle W, the radiation source control unit 41 uses the arrangement interval PT as the movement range and performs movement control in the movement range. Therefore, the unnecessary movement of the X-ray tube 36 can be suppressed.

As illustrated in FIG. 13, the radiation source control unit 41 performs control for equalizing the intervals of the focuses F corresponding to a plurality of projection images SP acquired by one tomosynthesis imaging operation. In a case in which the intervals of the focuses F are equalized, it is easy to perform calculation in the reconstruction of a tomographic image. As described with reference to FIG. 12, in the configuration in which the X-ray tubes 36 are linearly arranged as in this example, even in a case in which the arrangement interval PT of the X-ray tubes 36 is equal, the angle PA corresponding to the arrangement interval PT is not equal and the angle PA corresponding to the arrangement interval PT is gradually reduced from the center toward both ends. However, in a case in which the arrangement interval PT is equal, the change rate of the angle PA is regular. Therefore, a plurality of irradiation angles SA corresponding to a plurality of projection images SP acquired in one tomosynthesis imaging operation are changed regularly. As a result, it is easy to perform calculation in the reconstruction of a tomographic image, as compared to a case in which a plurality of irradiation angles SA are randomly changed.

In addition, control may be performed such that a plurality of focuses F are arranged symmetrically with respect to the center CP. In this case, a plurality of acquired projection images SP include a plurality of sets of projection images SP having bilaterally symmetric angles, which makes it easy to perform calculation.

A fixed anode type in which the anode 52 is a fixed anode is used as the X-ray tube 36. The fixed anode type can be miniaturized because it does not have a rotating structure in a rotating anode type. In a case in which a plurality of X-ray tubes 36 are used, the overall size of the X-ray source 24 tends to be larger than that in a case in which one X-ray tube 36 is used. Therefore, in a case in which the size of the X-ray tube 36 is reduced, the size of the X-ray source 24 is also reduced, which is greatly advantageous. In addition, in a case in which the plurality of X-ray tubes 36 are arranged as in this example, as the diameter of the X-ray tube 36 becomes smaller, the arrangement interval PT of the X-ray tubes 36 can become shorter. Therefore, it is possible to further increase the density of the irradiation positions in the range of the scanning angle KA.

Further, an X-ray tube 36 having a field-emission-type cathode 51 is used as the X-ray tube 36. The field-emission-type cathode 51 is a cold cathode type and generates a smaller amount of heat than a hot cathode type which heats a filament to emit thermal electrons. Therefore, since the number of members for heat countermeasures is reduced, it is easy to reduce the size of the X-ray tube 36. The advantages of reducing the size of the X-ray tube 36 are as described above.

In the above-mentioned example, the X-ray source 24 includes nine X-ray tubes 36. However, the number of X-ray tubes 36 in the X-ray source 24 may be equal to or greater than two or equal to or less than eight or may be equal to or greater than ten.

For the irradiation order of the plurality of X-ray tubes 36, irradiation may not be sequentially performed from the X-ray tube 36 disposed at one end in the arrangement direction. The irradiation order can be changed in various ways. For example, irradiation may be randomly performed such that the X-ray tube 36 disposed at the center emits radiation and then the X-ray tube 36 disposed at one end emits radiation. In addition, the irradiation order at each stop position may be changed.

Of course, the effect of simplifying the irradiation order control can be obtained by setting the same irradiation order at each stop position and directing the plurality of X-ray tubes 36 to sequentially emit X-rays from one end to the other end as in the above-mentioned example.

In the mammography apparatus 10, during one tomosynthesis imaging operation, the position and posture of the X-ray detector 26 are fixed. Since only the X-ray tubes 36 are moved, a movement mechanism and movement control are simple.

Figure 15:
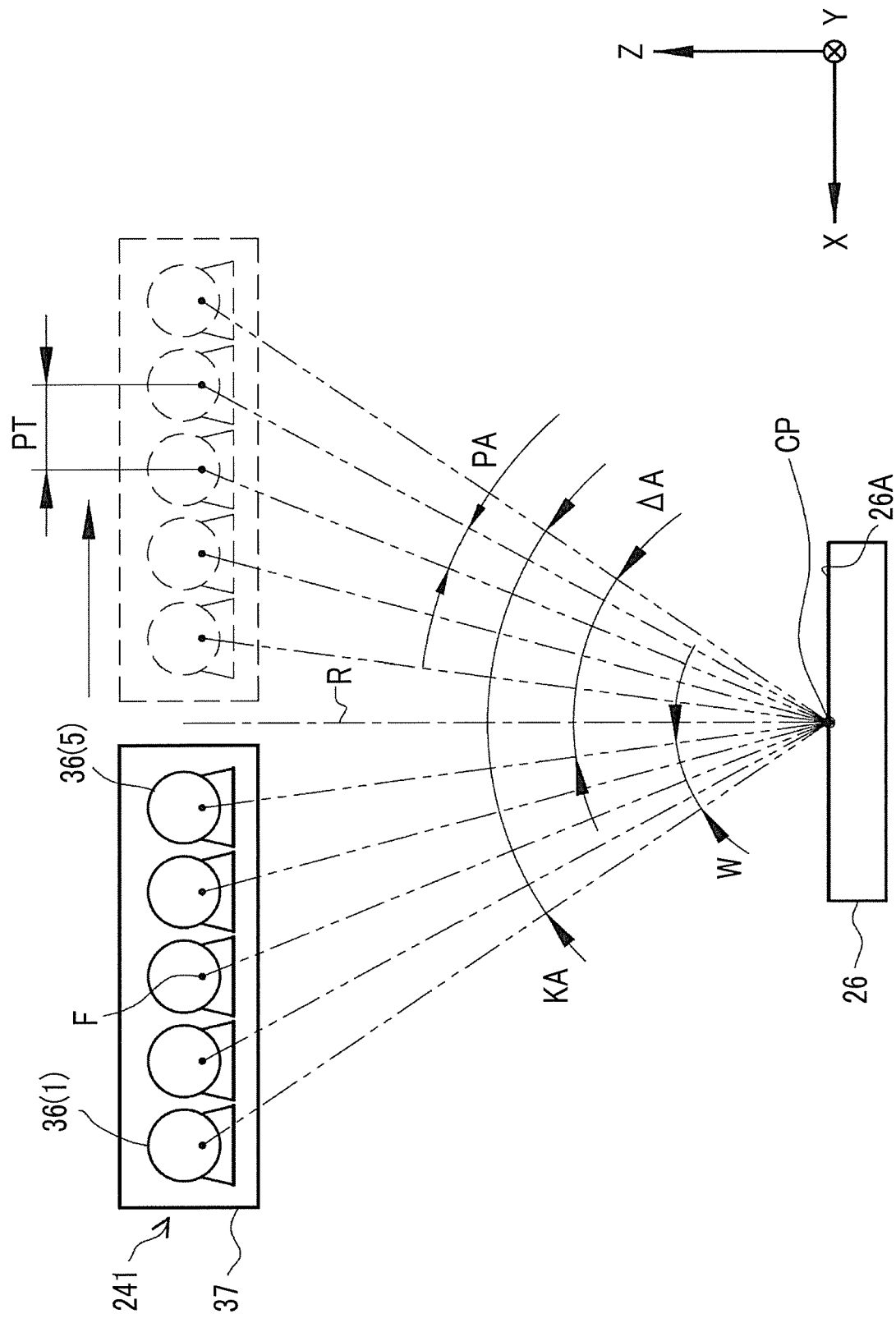
FIG. 15 is a diagram illustrating an example of a case in which a spread angle is less than a scanning angle.

Movement Range of X-ray Source Corresponding to Scanning Angle KA and Spread Angle W In the above-mentioned example, the case in which the scanning angle KA is equal to or less than the spread angle W (KA≤W) has been described. However, as illustrated in FIG. 15, there is a case in which the scanning angle KA is greater than the spread angle W (KA>W). An X-ray source 241 illustrated in FIG. 15 includes five X-ray tubes 36 and a housing 37. As such, even in a case in which the scanning angle KA is greater than the spread angle W (KA>W), the amount of movement of a plurality of X-ray tubes 36 is less than that in the related art in which tomosynthesis imaging is performed while one X-ray tube 36 is moved. Therefore, it is possible to reduce the imaging time while suppressing artifacts in a tomographic image, as compared to the related art.

It is assumed that the remaining angle obtained by subtracting the spread angle W of the X-ray source 241 from the scanning angle KA is a difference ΔA as illustrated in FIG. 15. In the example illustrated in FIG. 15, the difference ΔA is equal to or greater than the angle PA corresponding to the arrangement interval PT (ΔA≥PA). In this case, as illustrated in FIG. 15, the X-ray source 241 is moved to a position represented by a dashed line to ensure the minimum amount of movement required to perform tomosynthesis imaging at the scanning angle KA. The movement control unit 41B sets the movement range of the plurality of X-ray tubes 36 in the range of the difference ΔA and performs movement control in the set range.

Figure 16:
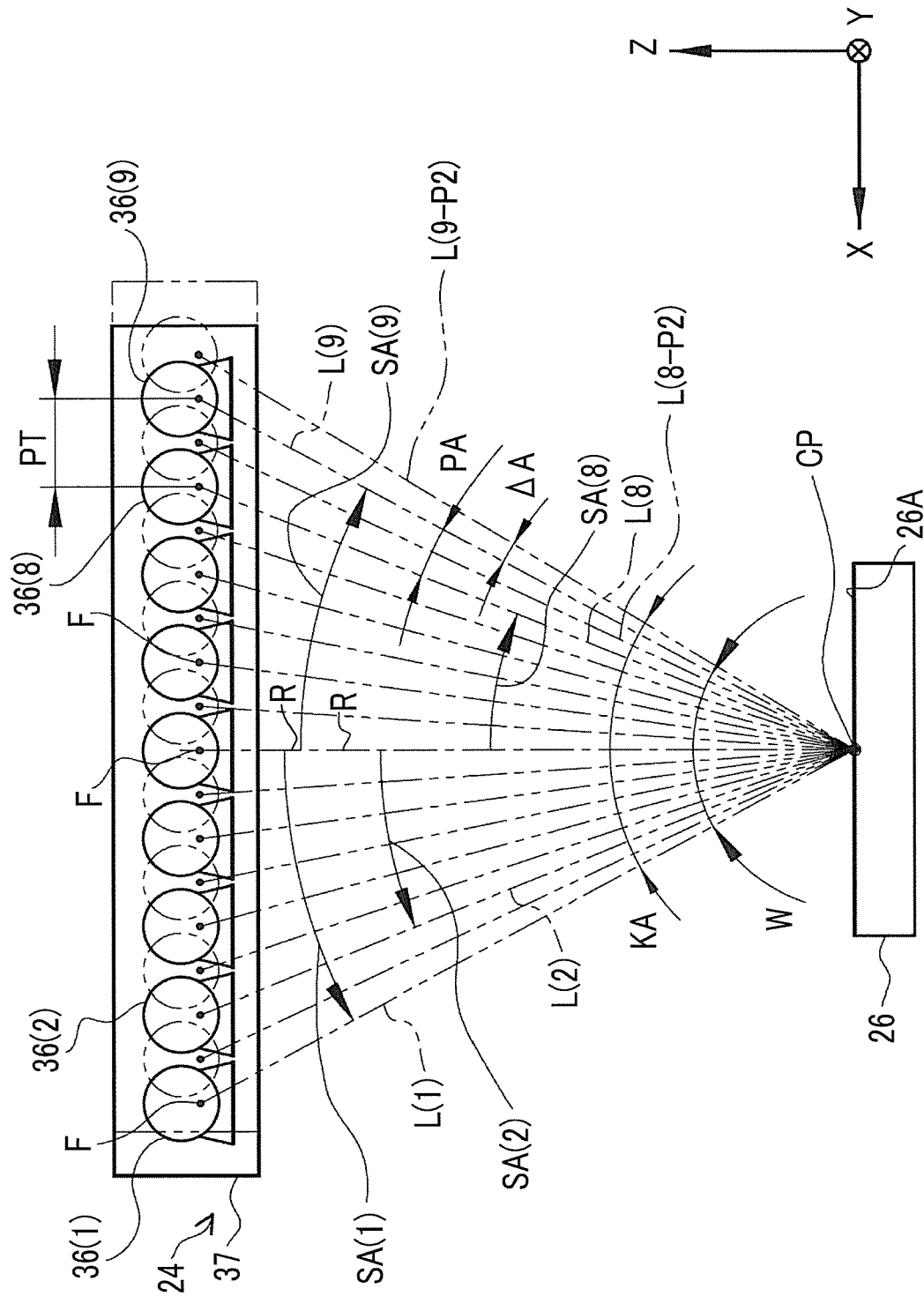
FIG. 16 is a diagram illustrating another example of the case in which the spread angle is less than the scanning angle.

As illustrated in FIG. 16, in a case in which the scanning angle KA is greater than the spread angle W (KA>W) similarly to the example illustrated in FIG. 15, the difference ΔA may be less than the angle PA corresponding to the arrangement interval PT (ΔA<PA) unlike the example illustrated in FIG. 15. In this case, the movement range of the plurality of X-ray tubes 36 is not set in the range of the difference ΔA, but is set in the range of the arrangement interval PT, similarly to the case in which the scanning angle KA illustrated in FIG. 13 is equal to or less than the spread angle W (KA≤W).

The reason is as follows. In a case in which the difference ΔA is less than the angle PA corresponding to the arrangement interval PT (ΔA<PA) as illustrated in FIG. 17, even though the difference ΔA is set as the movement range, there is a portion of a focus interval DG in which it is difficult to set the irradiation position.

Figure 17:
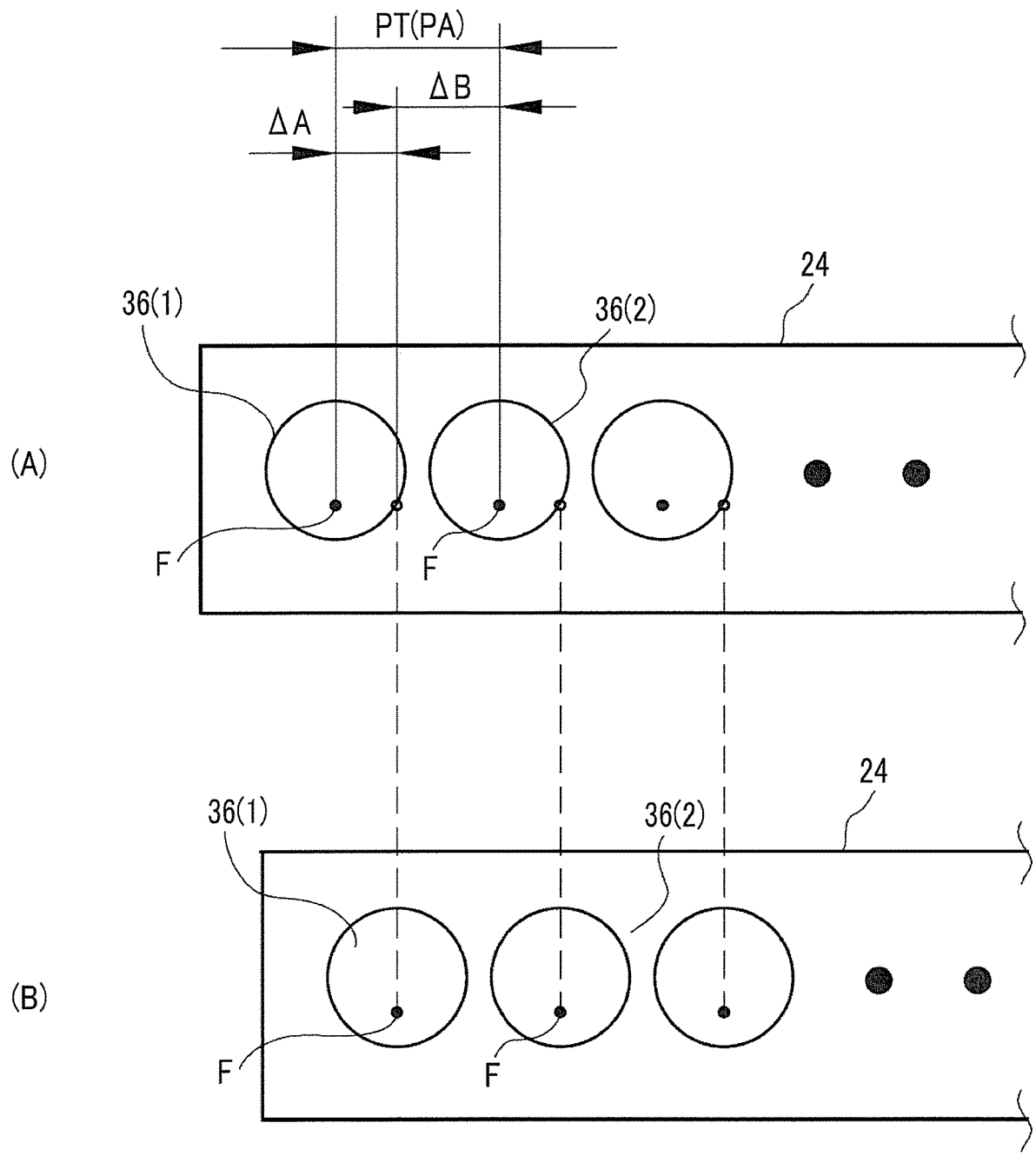
FIG. 17 is an enlarged view illustrating the example illustrated in FIG. 16. (A) of FIG. 17 is a diagram illustrating a first stop position of the plurality of X-ray tubes and (B) of FIG. 17 is a diagram illustrating a second stop position of the plurality of X-ray tubes.

In FIG. 17, (A) illustrates a plurality of X-ray tubes 36 (X-ray source 24) at the first stop position and (B) illustrates a plurality of X-ray tubes 36 (X-ray source 24) at the second stop position. In FIG. 17, the movement range is the difference ΔA. Here, as described above, in a case in which the X-ray tubes 36 are linearly arranged, the angle PA corresponding to the arrangement interval PT is gradually reduced from the center toward both ends. Therefore, precisely, the arrangement interval PT is different from the angle PA corresponding to the arrangement interval PT. However, for the definition of the movement range, there is no problem in considering the maximum value of the angle PA to be equivalent to the arrangement interval PT. Therefore, in the description, the arrangement interval PT is considered to be equivalent to the maximum value of the angle PA.

In the example illustrated in FIG. 17, the difference ΔA is less than the arrangement interval PT (angle PA). Even in a case in which the X-ray source 24 is moved by the difference ΔA, it is difficult to set the irradiation position within the range of a difference ΔB between the arrangement interval PT (angle PA) and AA in the range of the focus interval DG. Therefore, as such, in a case in which the difference ΔA is less than the arrangement interval PT (angle PA), the movement range of a plurality of X-ray tubes 36 is set in the range of the arrangement interval PT (angle PA) similarly to the case illustrated in FIG. 13 in which the scanning angle KA is equal to or less than the spread angle W.

Summarizing the above, the movement range in the movement control performed by the movement control unit 41B is as follows.

First, in a case in which the scanning angle KA is equal to or less than the spread angle W (KA≤W) as illustrated in FIG. 13, the movement control unit 41B sets the movement range of a plurality of X-ray tubes 36 in the range of the arrangement interval PT and performs movement control.

Second, in a case in which the scanning angle KA is greater than the spread angle W (KA>W) and the difference ΔA is equal to or greater than the arrangement interval PT (angle PA) (ΔA≥PA) as illustrated in FIG. 15, the movement control unit 41B sets the movement range of a plurality of X-ray tubes 36 in the range of the difference ΔA and performs movement control.

Third, in a case in which the scanning angle KA is greater than the spread angle W (KA>W) and the difference ΔA is less than the arrangement interval PT (angle PA) (ΔA<PA) as illustrated in FIG. 16, the movement control unit 41B sets the movement range of a plurality of X-ray tubes 36 in the range of the arrangement interval PT and performs movement control.

Summarizing the second and third cases, in a case in which the scanning angle KA is greater than the spread angle W (KA>W), the movement control unit 41B compares the difference ΔA and the arrangement interval PT (angle PA), sets the movement range in the larger of the two, and performs movement control.

It is possible to obtain the minimum necessary movement range by setting the movement range of the plurality of X-ray tubes 36 (the X-ray source 24 or the X-ray source 241) to the above-mentioned movement range. Therefore, it is possible to suppress the unnecessary movement of the plurality of X-ray tubes 36 (the X-ray source 24 or the X-ray source 241).

Second Embodiment

Figure 18:
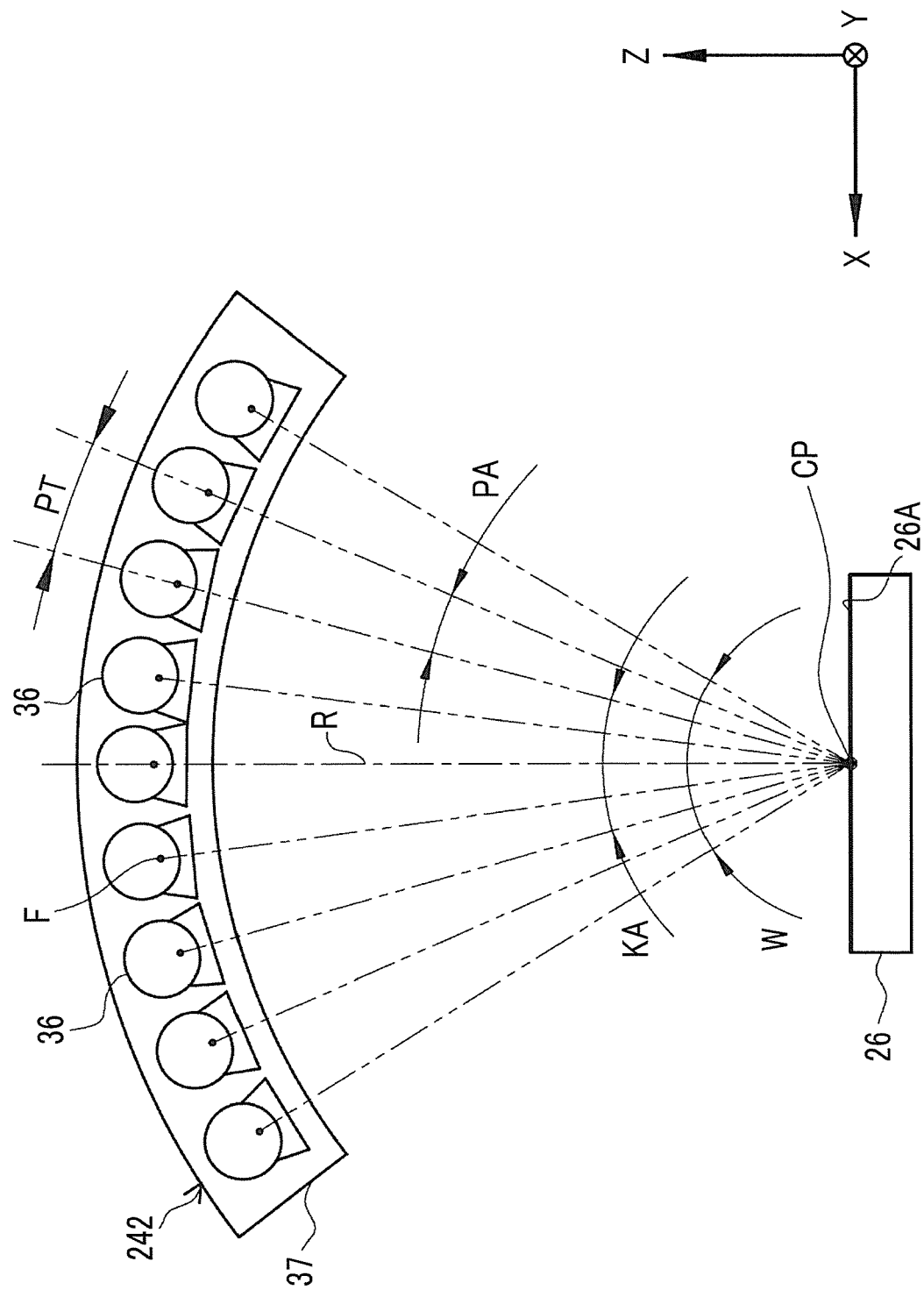
FIG. 18 is a diagram illustrating a plurality of X-ray tubes arranged in an arc shape.
Figure 19:
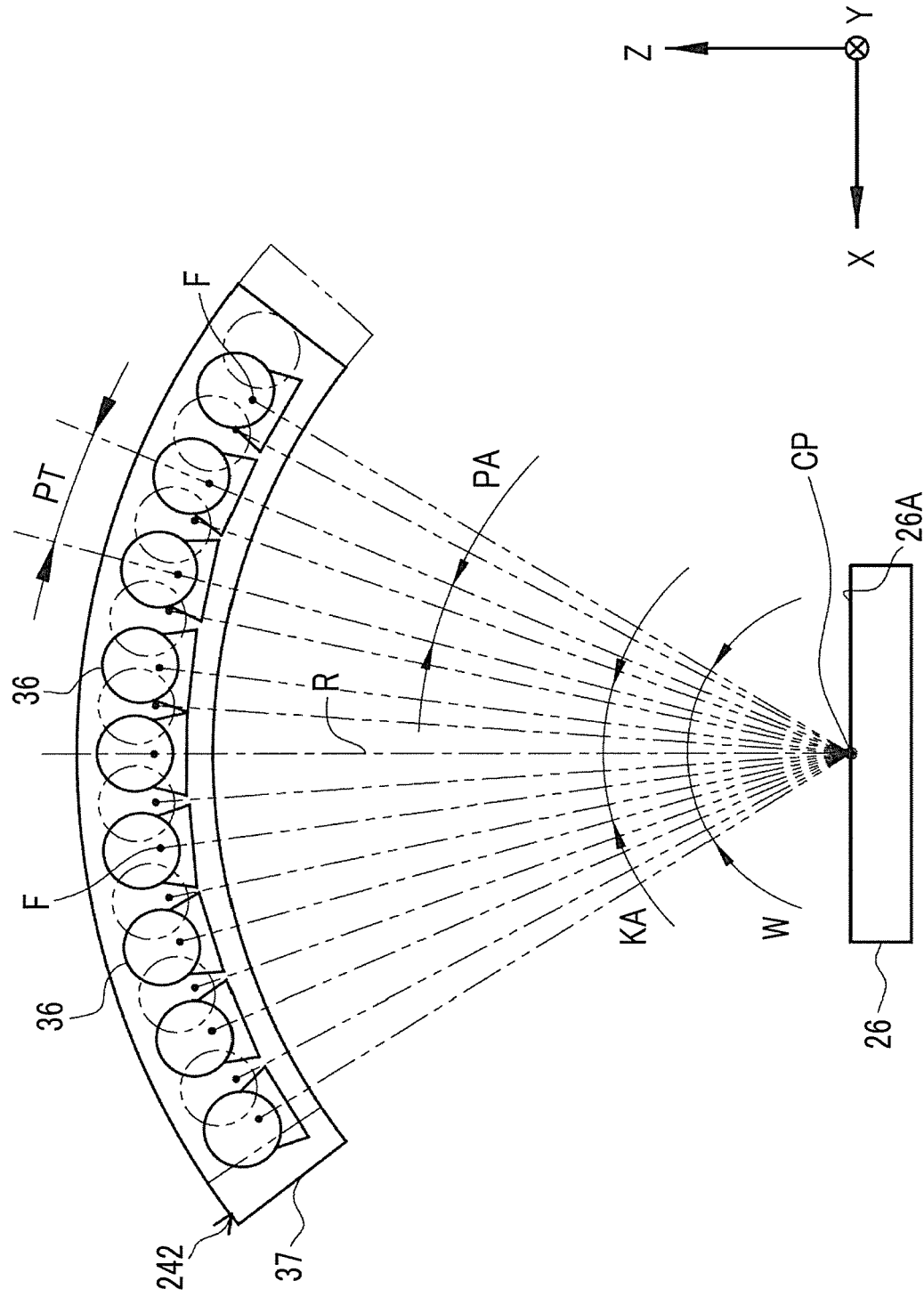
FIG. 19 is a diagram illustrating an aspect in which the plurality of X-ray tubes illustrated in FIG. 18 are moved.

FIGS. 18 and 19 illustrate an X-ray source 242 according to a second embodiment. In the second embodiment, the description of the same points as those in the first embodiment will not be repeated and the difference from the first embodiment will be mainly described. In the X-ray source 242, a plurality of X-ray tubes 36 are arranged in an arc shape at equal intervals as viewed from the direction parallel to the imaging surface 26A. In the X-ray source 242 according to the second embodiment, similarly to the X-ray source 24 according to the first embodiment in which the X-ray tubes 36 are linearly arranged, the X-ray tubes 36 are arranged in a line in a plan view from the Z direction perpendicular to the imaging surface 26A. However, in the X-ray source 242, the plurality of X-ray tubes 36 are arranged in a convex arc shape in which the center in the arrangement direction in a plan view from the Z direction protrudes in a direction away from the imaging surface 26A. This is different from the X-ray source 24 according to the first embodiment.

In the case of the X-ray source 242 in which the plurality of X-ray tubes 36 are arranged in an arc shape, the arrangement interval PT of each X-ray tube 36 is equal to the angle PA corresponding to the arrangement interval PT unlike the X-ray source 24 according to the first embodiment in which the plurality of X-ray tubes 36 are linearly arranged.

In a case in which the movement control unit 41B moves the X-ray source 242 as illustrated in FIG. 19, the X-ray source 242 is rotated on the center CP of the imaging surface 26A as a rotation center along the arc-shaped arrangement of the X-ray source 242. Then, the plurality of X-ray tubes 36 are moved on an arc-shaped trajectory. In the second embodiment, the movement control unit 41B sets the movement range of the plurality of X-ray tubes 36 to the same range as that in the first embodiment. In the example illustrated in FIG. 19, since the scanning angle KA is equal to or less than the spread angle W (KA W), the movement control unit 41B sets the movement range in the range of the arrangement interval PT and performs movement control.

In the second embodiment, the same movement control for equalizing the focus intervals as that in the first embodiment can be performed.

Third Embodiment

Figure 20:
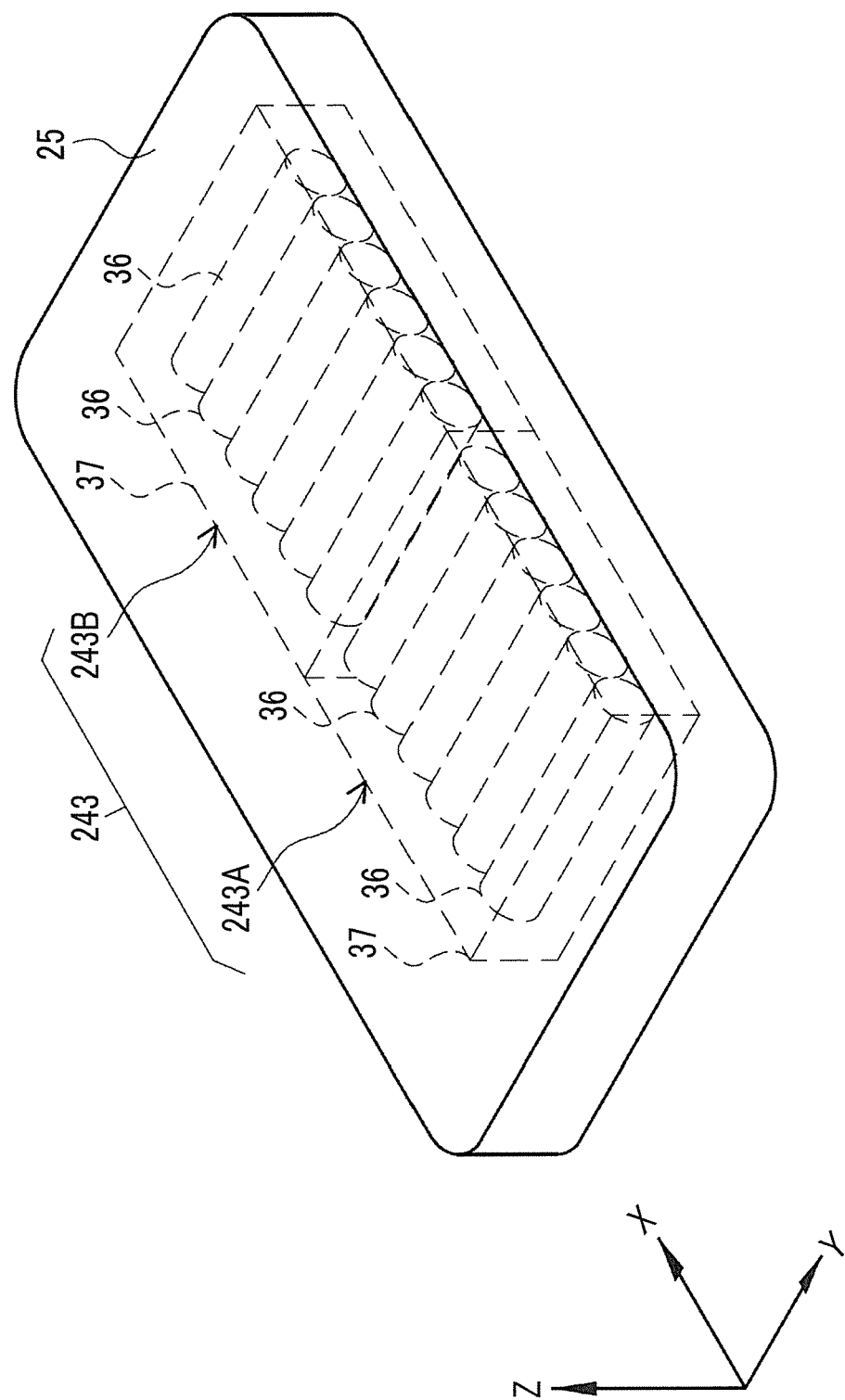
FIG. 20 a diagram illustrating an X-ray source divided into a plurality of units.

FIGS. 20 to 23 illustrate an X-ray source 243 according to a third embodiment. In the third embodiment, the description of the same points as those in the first embodiment will not be repeated and the difference from the first embodiment will be mainly described. As illustrated in FIG. 20, the X-ray source 243 includes two units, that is, a first unit 243A and a second unit 243B in which a plurality of X-ray tubes 36 are divided and accommodated. In this example, each of the first unit 243A and the second unit 243B includes six X-ray tubes 36 and a housing 37. The X-ray source 243 is accommodated in the radiation source accommodation portion 25 similarly to the X-ray source 24 according to the first embodiment.

As such, since the plurality of X-ray tubes 36 are divided and accommodated in a plurality of units, that is, the first unit 243A and the second unit 243B, for example, it is possible to replace only the unit accommodating a broken X-ray tube 36 and it is easy to perform maintenance.

Figure 21:
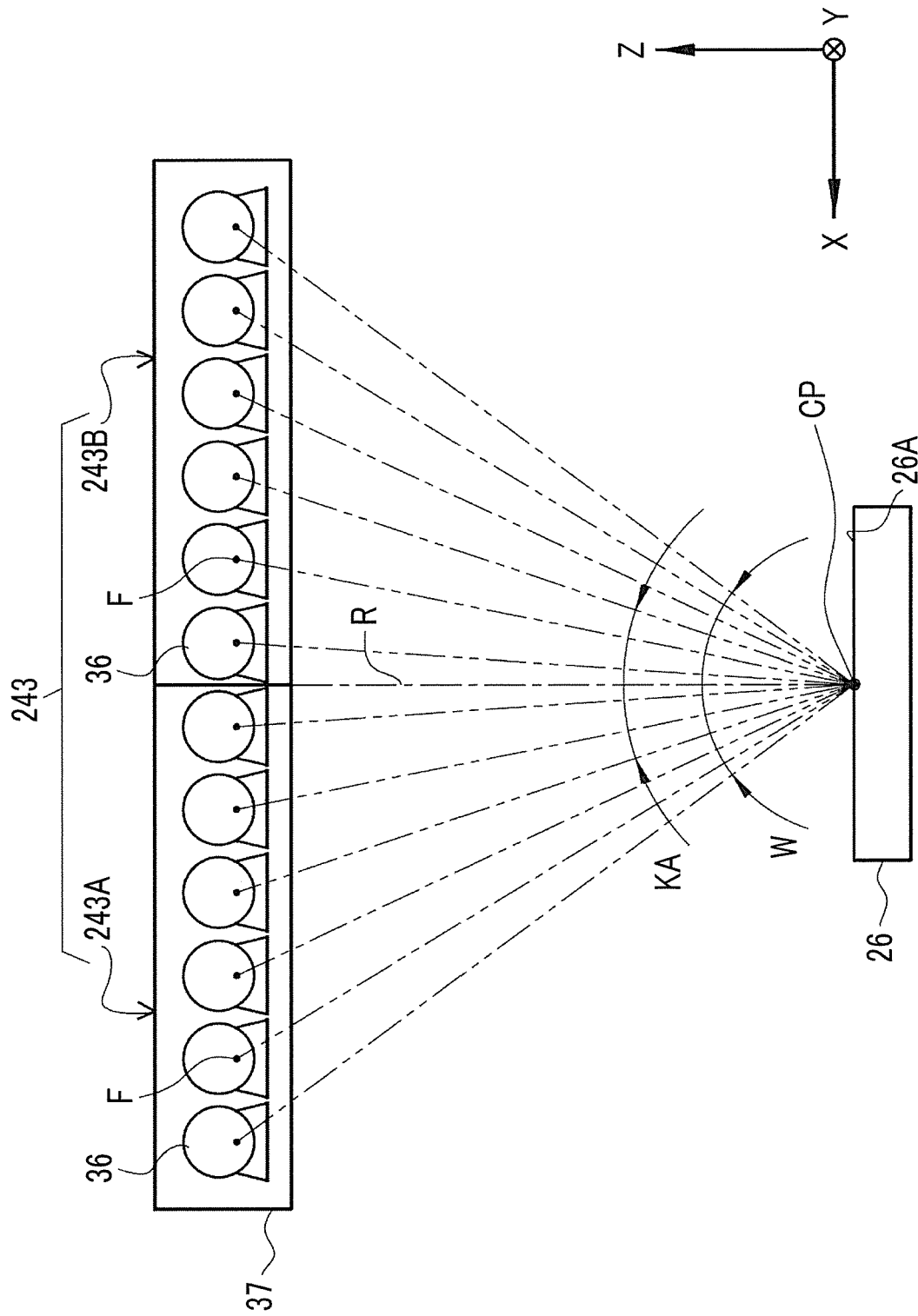
FIG. 21 is a diagram illustrating the irradiation position of the X-ray source divided into the plurality of units.

As illustrated in FIG. 21, in the first unit 243A and the second unit 243B, the X-ray tubes 36 are linearly arranged in a row along the X direction in a plane parallel to the imaging surface 26A similarly to the first embodiment. Therefore, similarly to the first embodiment, even in a state in which each X-ray tube 36 is stopped, it is possible to emit X-rays at a plurality of different irradiation angles SA.

Figure 22:
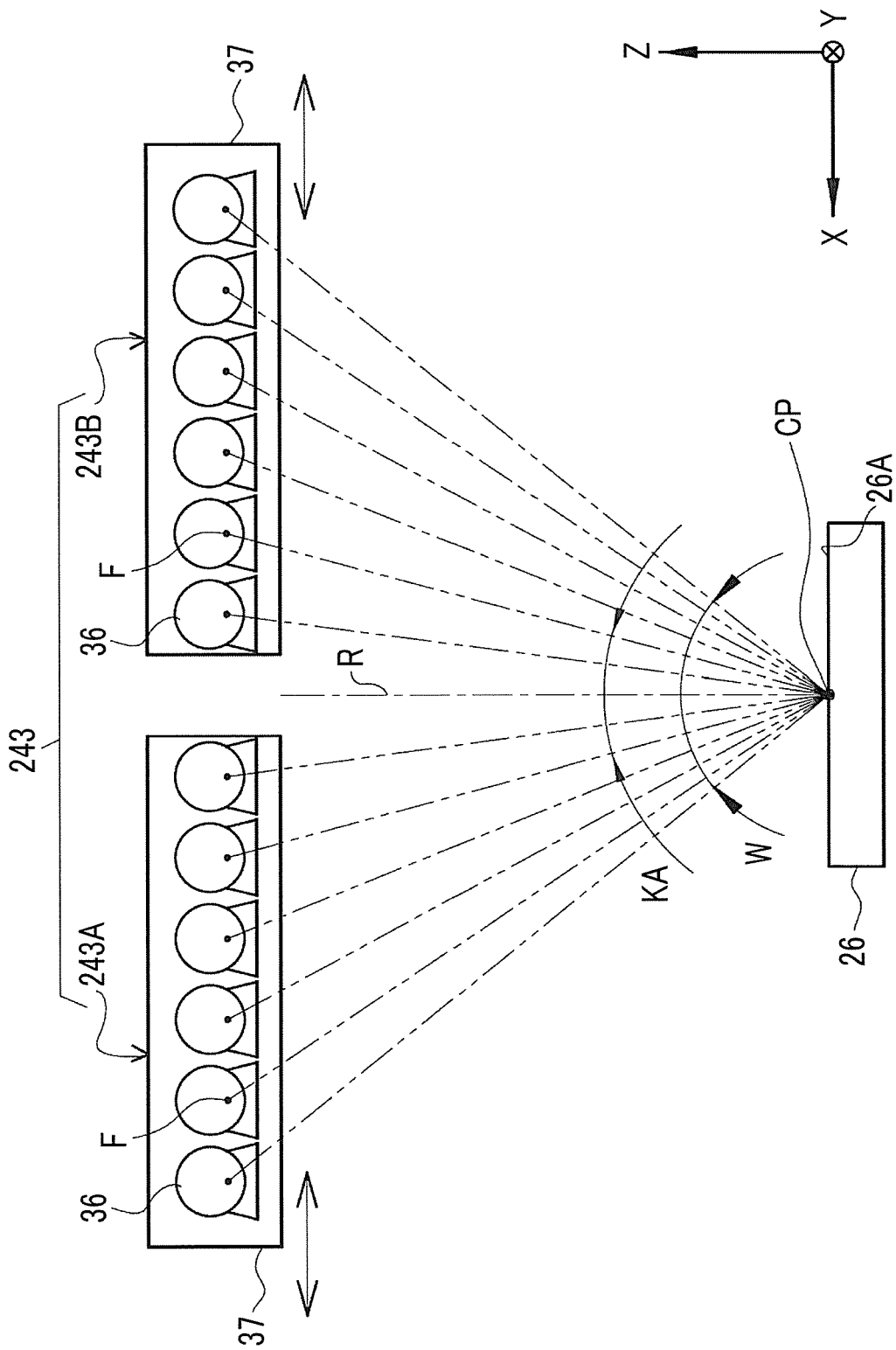
FIG. 22 is a diagram illustrating an aspect in which each unit of the X-ray source illustrated in FIG. 21 is moved.

As illustrated in FIG. 22, the first unit 243A and the second unit 243B can be moved along the arrangement direction (X direction). The movement control unit 41B can perform the same movement control as that in the first embodiment for the first unit 243A and the second unit 243B. The effect of increasing the density of the irradiation positions in the scanning angle KA is obtained by the movement control, which is the same as that in the first embodiment.

The movement control differs from that in the first embodiment in the following points. The movement control unit 41B of the radiation source control unit 41 can move each of the first unit 243A and the second unit 243B in the movement control. Therefore, the movement control unit 41B performs the following movement control in one tomosynthesis imaging operation.

Figure 23:
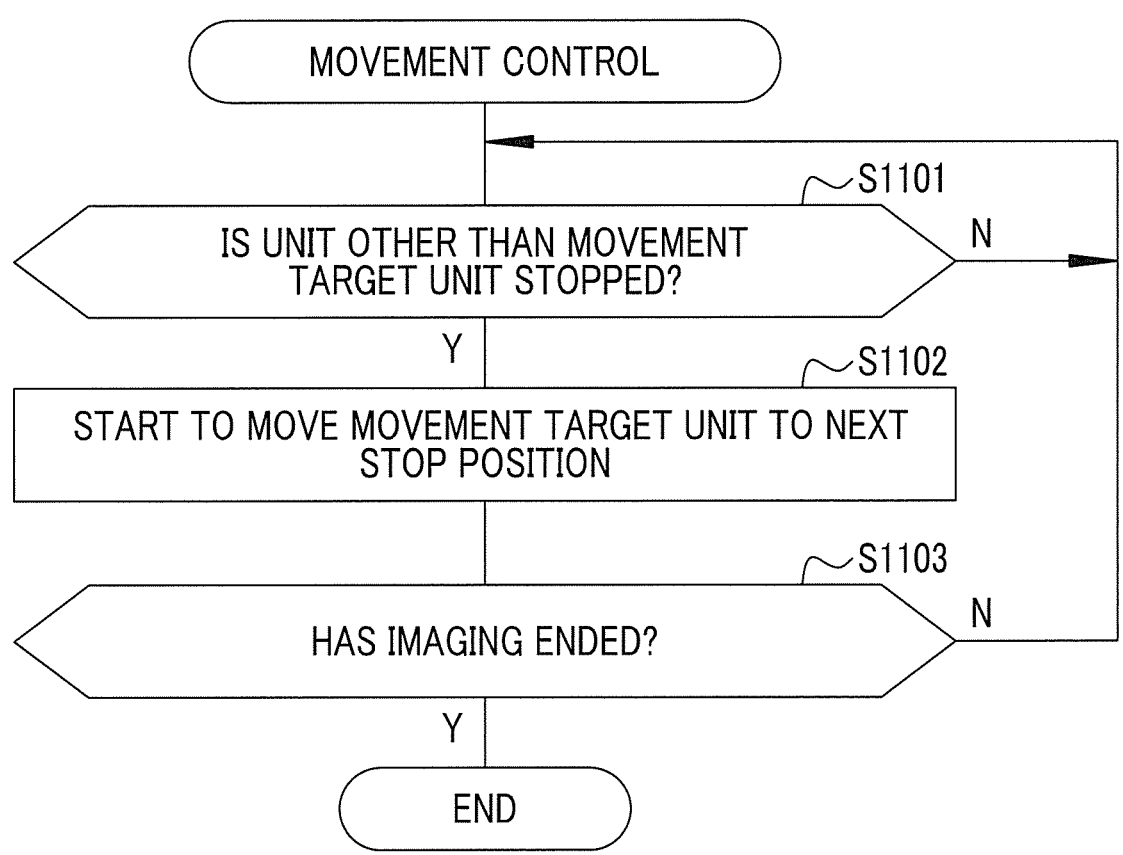
FIG. 23 is a flowchart illustrating the procedure of movement control for a plurality of units.

That is, as illustrated in FIG. 23, in the movement control, in a case in which a movement target unit to be moved among a plurality of units is moved to the next stop position for irradiation, in Step S1101, the movement control unit 41B determines whether a unit other than the movement target unit is stopped for irradiation. In a case in which it is determined that the unit other than the movement target unit is stopped (Y in Step S1101), the movement control unit 41B proceeds to Step S1102 and starts to move the movement target unit to the next stop position for irradiation while the unit other than the movement target unit is stopped. As described above, in the movement control, the stop, irradiation, and movement of a plurality of X-ray tubes 36 are repeated. The movement control unit 41B repeats this process until tomosynthesis imaging ends (Y in Step S1103) (N in Step S1103).

Specifically, in a case in which the first unit 243A is the movement target unit in the X-ray source 243 illustrated in FIG. 22, it is determined that the second unit 243B is stopped for irradiation. In a case in which the second unit 243B is stopped, the movement of the first unit 243A to the next stop position starts. This movement control is performed to overlap the imaging timing of one unit with the movement timing of the other unit. Therefore, the overall imaging time of tomosynthesis imaging can be shorter than that in a case in which the imaging timing and the movement timing do not overlap each other.

In this example, the plurality of X-ray tubes 36 are divided and accommodated in two units. However, the number of units may be equal to or greater than three. In addition, a plurality of X-ray tubes 36 may not be necessarily accommodated in each unit and at least one X-ray tube 36 may be accommodated in each unit. Of course, in a case in which a plurality of X-ray tubes 36 are accommodated in each unit, the number of housings 37 is reduced. Therefore, this configuration contributes to reducing the size and cost of the X-ray source. In addition, different numbers of X-ray tubes 36 may be accommodated in each unit. For example, five X-ray tubes 36 may be accommodated in one unit and six X-ray tubes 36 may be accommodated in another unit.

In this example, all of the plurality of X-ray tubes 36 are moved. For example, in a case in which the scanning angle KA is less than the spread angle W, it is sufficient to move the X-ray tubes 36 selected according to the scanning angle KA. Therefore, in a case in which a plurality of X-ray tubes 36 are divided into a plurality of units, all of the plurality of X-ray tubes 36 may not be moved or at least one selected X-ray tube 36 may be moved.

Others

Other Aspects of X-ray Tube

For example, in the first embodiment, the field-emission-type cold cathode is used as the cathode 51 of the X-ray tube 36. However, X-ray tubes other than the X-ray tube 36 may be used. For example, an X-ray tube including a hot cathode in which a filament is heated to emit thermal electrons may be used as the X-ray tube 36.

For example, the irradiation control of the X-ray tube including the hot cathode is performed as follows. First, a current flows to the filament to heat the filament. In this state, a high voltage is applied between the hot cathode and the anode. Then, thermal electrons are emitted from the hot cathode.

Other Aspects of Tomosynthesis Imaging Apparatus

In the above-described embodiments, the mammography apparatus 10 has been described as an example of the tomosynthesis imaging apparatus. In mammography, since the usability of tomosynthesis imaging is recognized, it is preferable to apply the tomosynthesis imaging apparatus according to the present disclosure to the mammography apparatus 10. Of course, the tomosynthesis imaging apparatus is not limited to the mammography apparatus 10 and may be applied to other imaging apparatuses.

For example, as illustrated in FIG. 24, the tomosynthesis imaging apparatus according to the present disclosure may be applied to an imaging apparatus 100 in addition to the mammography apparatus 10. The imaging apparatus 100 illustrated in FIG. 27 is an X-ray imaging apparatus that captures the image of a subject H during surgery.

The imaging apparatus 100 includes a main body 101 having a control device provided therein and a C-arm 102. The main body 101 is provided with a carriage 103. The C-arm 102 is provided with a radiation source accommodation portion 104 and a detector accommodation portion 106. The radiation source accommodation portion 104 and the detector accommodation portion 106 are held at the posture where they face each other as in the first embodiment.

The detector accommodation portion 106 is inserted below a bed 107 on which the subject H lies supine. The bed 107 is made of a material that transmits X-rays. The radiation source accommodation portion 104 is provided above the subject H at a position that faces the detector accommodation portion 106 with the subject H interposed therebetween.

An X-ray source 244 including a plurality of X-ray tubes 36 which is the same as the X-ray source 24 according to the first embodiment is provided in the radiation source accommodation portion 104. Since the imaging range of the imaging apparatus 100 is wider than the range of the breast BR, the size of the X-ray tube 36 may be larger than the size of the X-ray tube 36 of the X-ray source 24 in the mammography apparatus 10 or the number of X-ray tubes 36 may be larger than that in the mammography apparatus 10.

The imaging apparatus 100 can perform the same movement control as that for the X-ray source 24 according to the first embodiment for the X-ray source 244 to perform tomosynthesis imaging.

In the imaging apparatus 100, similarly to the mammography apparatus 10, it is possible to perform simple X-ray imaging in addition to tomosynthesis imaging. In addition, instead of performing the simple X-ray imaging, a composite two-dimensional image may be generated. Further, the imaging apparatus 100 may capture moving X-ray images in addition to still X-ray images.

The tomosynthesis imaging apparatus according to the present disclosure may be applied to a general X-ray imaging apparatus configured by combining a ceiling-suspended X-ray source and an upright imaging table or a decubitus imaging table in addition to the imaging apparatus 100 for surgery. Further, the tomosynthesis imaging apparatus may be applied to, for example, a cart-type mobile X-ray imaging apparatus which is moved to each hospital room and is used to capture the image of a patient.

In the above-described embodiments, for example, the following various processors can be used as the hardware structure of processing units performing various processes, such as the radiation source control unit (the irradiation control unit and the movement control unit), the detector control unit, and the image processing unit. The various processors include a CPU which is a general-purpose processor executing software (program) to function as various processing units, a programmable logic device (PLD), such as a field programmable gate array (FPGA), whose circuit configuration can be changed after manufacture, and a dedicated electric circuit, such as an application specific integrated circuit (ASIC), which is a processor having a dedicated circuit configuration designed to perform a specific process.

The various processes may be performed by one of the various processors or a combination of two or more processors of the same type or different types (for example, a combination of a plurality of FPGAs and a combination of a CPU and an FPGA). In addition, a plurality of processing units may be configured by one processor. An example of the configuration in which a plurality of processing units are configured by one processor is an aspect in which a processor that implements the functions of the entire system including a plurality of processing units using one integrated circuit (IC) chip is used. An example of this aspect is a system-on-chip (SoC).

As such, various processing units are configured by using one or more of the various processors as a hardware structure.

In addition, specifically, an electric circuit (circuitry) obtained by combining circuit elements, such as semiconductor elements, can be used as the hardware structure of the various processors.

In the technology according to the present disclosure, the above-mentioned various embodiments or various modification examples may be combined with each other. In the above-described embodiments, the imaging apparatus using X-rays as radiation have been described as an example. However, an imaging apparatus using γ-rays may be described as an example. In addition, the present disclosure is not limited to the above-described embodiments and various configurations can be used without departing from the scope and spirit of the present disclosure.

What is claimed is:

1. A tomosynthesis imaging apparatus comprising:
a radiation detector having an imaging surface that detects radiation transmitted through an object and captures a projection image of the object;
a radiation source that has a plurality of radiation tubes which emit the radiation to the imaging surface at different irradiation angles and selectively irradiates the object with the radiation from the plurality of radiation tubes; and
a radiation source control unit that performs movement control for moving at least one of the plurality of radiation tubes to change the radiation irradiation angle of the radiation tube with respect to the imaging surface,
wherein, in one tomosynthesis imaging operation that selectively performs the emission of the radiation from the plurality of radiation tubes to acquire a plurality of the projection images based on the emission of the radiation from each radiation tube,
wherein, assuming that the irradiation angle is an angle formed between a normal line to the imaging surface which extends from a center of the imaging surface and a segment which connects the center of the imaging surface and a focus of each of the plurality of radiation tubes; the plurality of radiation tubes arranged in a row are N radiation tubes; the radiation tube disposed at one end in the arrangement direction is a first radiation tube; the radiation tube disposed at the other end is an N-th radiation tube; a segment which connects the center of the imaging surface and the focus of the first radiation tube is a first segment; a segment which connects the center of the imaging surface and the focus of the N-th radiation tube is an N-th segment; an angle formed between the first segment and the N-th segment is a spread angle W in the arrangement direction of the plurality of radiation tubes; a sum of absolute values of maximum irradiation angles in a positive direction and a negative direction from the normal line among a plurality of the irradiation angles corresponding to the plurality of projection images acquired in the one tomosynthesis imaging operation is a scanning angle KA of the radiation source required for the one tomosynthesis imaging operation; an arrangement interval of the plurality of radiation tubes is PT; and a remaining angle obtained by subtracting the spread angle W from the scanning angle KA is a difference $\Delta A$,
in a case in which KA≤W is satisfied, the radiation source control unit sets a movement range in a range of PT and performs the movement control, and
in a case in which KA>W is satisfied, the radiation source control unit sets the movement range in a range of the larger of $\Delta A$ and PT and performs the movement control.

2. The tomosynthesis imaging apparatus according to claim 1,
wherein the plurality of radiation tubes are arranged in a row in the radiation source.

3. The tomosynthesis imaging apparatus according to claim 2,
wherein, the radiation source control unit performs irradiation control for controlling an irradiation order of the selected radiation tubes among the plurality of radiation tubes and movement control for the selected radiation tubes among the plurality of radiation tubes.

4. The tomosynthesis imaging apparatus according to claim 1,
wherein, in a case in which the number of the plurality of radiation tubes is N and the number of stop positions where the plurality of radiation tubes emit the radiation in the movement range is Np, the radiation source control unit is capable of directing the plurality of radiation tubes to emit the radiation a total of Mp (=N×Np) times in the one tomosynthesis imaging operation.

5. The tomosynthesis imaging apparatus according to claim 1,
wherein
the radiation source control unit performs control for equalizing the intervals between the focuses corresponding to the plurality of projection images acquired in the one tomosynthesis imaging operation.

6. The tomosynthesis imaging apparatus according to claim 1,
wherein the radiation source includes a plurality of units in which the plurality of radiation tubes are divided and accommodated.

7. The tomosynthesis imaging apparatus according to claim 6,
wherein the radiation source control unit is capable of moving each of the plurality of units in the movement control, and
in the one tomosynthesis imaging operation, in a case in which at least one movement target unit to be moved among the plurality of units is moved to a next stop position for irradiation, the radiation source control unit starts to move the movement target unit while a unit other than the movement target unit is stopped for irradiation.

8. The tomosynthesis imaging apparatus according to claim 1,
wherein a position and posture of the radiation detector are fixed during imaging.

9. The tomosynthesis imaging apparatus according to claim 1,
wherein the object is a breast.

10. The tomosynthesis imaging apparatus according to claim 1,
wherein the radiation tube includes a cathode that emits electrons and an anode that emits radiation from a focus where the electrons emitted from the cathode collide.

11. The tomosynthesis imaging apparatus according to claim 10,
wherein the anode is a fixed anode.

12. The tomosynthesis imaging apparatus according to claim 10,
wherein the cathode is a field emission type that emits electrons using a field emission phenomenon which occurs in a case in which an electric field is applied to a surface of a conductor.

13. The tomosynthesis imaging apparatus according to claim 2,
wherein, in the radiation source, the plurality of radiation tubes are linearly arranged in a plane parallel to the imaging surface.

14. The tomosynthesis imaging apparatus according to claim 2,
wherein, in the radiation source, the plurality of radiation tubes are arranged in a convex arc shape in which a center in the arrangement direction of the radiation tubes protrudes in a direction away from the imaging surface.

15. The tomosynthesis imaging apparatus according to claim 1, further comprising:
an image processing unit that reconstructs a tomographic image of the object on the basis of the plurality of projection images.

16. A method for operating a tomosynthesis imaging apparatus comprising a radiation detector having an imaging surface that detects radiation transmitted through an object and captures a projection image of the object, the method comprising:
a radiation source control step including irradiation control for controlling a radiation source including a plurality of radiation tubes which emit the radiation to the imaging surface at different irradiation angles such that the plurality of radiation tubes selectively irradiate the object with the radiation and movement control for moving at least one of the plurality of radiation tubes to change the radiation irradiation angle of the radiation tube with respect to the imaging surface; and
an acquisition step of allowing the radiation detector to acquire a plurality of the projection images with different irradiation angles while performing the radiation source control step,
wherein, in one tomosynthesis imaging operation that selectively performs the emission of the radiation from the plurality of radiation tubes to acquire a plurality of the projection images based on the emission of the radiation from each radiation tube,
wherein, assuming that the irradiation angle is an angle formed between a normal line to the imaging surface which extends from a center of the imaging surface and a segment which connects the center of the imaging surface and a focus of each of the plurality of radiation tubes; the plurality of radiation tubes arranged in a row are N radiation tubes; the radiation tube disposed at one end in the arrangement direction is a first radiation tube; the radiation tube disposed at the other end is an N-th radiation tube;
a segment which connects the center of the imaging surface and the focus of the first radiation tube is a first segment; a segment which connects the center of the imaging surface and the focus of the N-th radiation tube is an N-th segment; an angle formed between the first segment and the N-th segment is a spread angle W in the arrangement direction of the plurality of radiation tubes; a sum of absolute values of maximum irradiation angles in a positive direction and a negative direction from the normal line among a plurality of the irradiation angles corresponding to the plurality of projection images acquired in the one tomosynthesis imaging operation is a scanning angle KA of the radiation source required for the one tomosynthesis imaging operation; an arrangement interval of the plurality of radiation tubes is PT; and a remaining angle obtained by subtracting the spread angle W from the scanning angle KA is a difference ΔA,
in a case in which KA≤W is satisfied, sets a movement range in a range of PT and performs the movement control in the radiation source control step, and
in a case in which KA>W is satisfied, sets the movement range in a range of the larger of ΔA and PT and performs the movement control in the radiation source control step.

17. A tomosynthesis imaging apparatus comprising:
a radiation detector having an imaging surface that detects radiation transmitted through an object and captures a projection image of the object;
a radiation source that has a plurality of radiation tubes which emit the radiation to the imaging surface at different irradiation angles and selectively irradiates the object with the radiation from the plurality of radiation tubes; and
a radiation source control unit that performs movement control for moving at least one of the plurality of radiation tubes to change the radiation irradiation angle of the radiation tube with respect to the imaging surface,
wherein, in one tomosynthesis imaging operation that selectively performs the emission of the radiation from the plurality of radiation tubes to acquire a plurality of the projection images based on the emission of the radiation from each radiation tube,
wherein the radiation source includes a plurality of units in which the plurality of radiation tubes are divided and accommodated,
wherein the radiation source control unit is configured to move each of the plurality of units in the movement control, and
in the one tomosynthesis imaging operation, in a case in which at least one movement target unit to be moved among the plurality of units is moved to a next stop position for irradiation, the radiation source control unit starts to move the movement target unit while a unit other than the movement target unit is stopped for irradiation.

* * * * *